(12) United States Patent
Leng et al.

(10) Patent No.: US 10,000,807 B2
(45) Date of Patent: Jun. 19, 2018

(54) MATERIALS AND METHODS FOR IDENTIFYING GYRASE INHIBITORS

(71) Applicants: Fenfei Leng, Palmetto Bay, FL (US); Xiaoduo Zhi, Volo, IL (US); Samantha Dages, Miami, FL (US); Kelley Dages, Miami, FL (US)

(72) Inventors: Fenfei Leng, Palmetto Bay, FL (US); Xiaoduo Zhi, Volo, IL (US); Samantha Dages, Miami, FL (US); Kelley Dages, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 0 days. days.

(21) Appl. No.: 15/254,553

(22) Filed: Sep. 1, 2016

(65) Prior Publication Data
US 2018/0057877 A1  Mar. 1, 2018

(51) Int. Cl.
*C12Q 1/6876* (2018.01)
*C12N 15/70* (2006.01)
*C12N 9/90* (2006.01)
*C12Q 1/66* (2006.01)
*C12Q 1/68* (2018.01)

(52) U.S. Cl.
CPC ............ *C12Q 1/6876* (2013.01); *C12N 9/90* (2013.01); *C12N 15/70* (2013.01); *C12Q 1/66* (2013.01); *C12Y 599/01003* (2013.01); *C12Q 2600/158* (2013.01)

(58) Field of Classification Search
None
See application file for complete search history.

(56) References Cited

U.S. PATENT DOCUMENTS

2003/0186292 A1* 10/2003 MacNeil ............... C12N 15/11
506/10

OTHER PUBLICATIONS

Menne et al., Expression studies with the bidirectional pcbAB-pcbC promoter region from Acremonium chrysogenum using reporter gene fusions; Appl. Microbiol Biotechnol, vol. 42, pp. 57-66, 1994.*
Higgins et al., A Physiological Role for DNA Supercoiling in the Osmotic Regulation of Gene Expression in *S. typhimurium* and *E. coli*; Cell, vol. 52, pp. 569-584, 1988.*
Appleman, J.A. et al., "Activation of *Escherichia coli* rRNA transcription by FIS during a growth cycle," *J. Bacteriol.*, 1998, 180:1525-1532.
Beck, C.F. et al., "Divergent promoters, a common form of gene organization," *Microbiol. Rev.*, 1988, 52:318-326.
Chen, D. et al., "Activity of a plasmid-borne leu-500 promoter depends on the transcription and translation of an adjacent gene," *Proc. Natl. Acad. Sci. U. S. A*, 1992, 89:8784-8788.
Chen, C.C. et al., "Transcription-driven DNA supercoiling and gene expression control," *Front Biosci.*, 2003, 8, d430-d439.
Collin, F. et al., "Exploiting bacterial DNA gyrase as a drug target: current state and perspectives," Appl Microbiol Biotechnol, 2011, 92:479-497.
Core, L.J. et al., "Nascent RNA sequencing reveals widespread pausing and divergent initiation at human promoters," *Science*, 2008, 322:1845-1848.
Deneke, J. et al., "The protelomerase of temperate *Escherichia coli* phage N15 has cleaving-joining activity," *Proc. Natl. Acad. Sci. U. S. A.*, 2000, 97:7721-7726.
Dennis, P.P. et al., "Control of rRNA synthesis in *Escherichia coli*: a systems biology approach," *Microbiol. Mol. Biol. Rev.*, 2004, 68, 639-668.
Dubnau, E. et al., "Suppression of promoter mutations by the pleiotropic supX mutations," *Mol. Gen. Genet.*, 1972, 117:91-112.
Duttke, S.H. et al., "Human promoters are intrinsically directional," *Mol. Cell.*, 2015, 57:674-684.
El Hanafi, H.D. et al., "Activation and silencing of *leu*-500 promoter by transcription-induced DNA supercoiling in the *Salmonella* chromosome," *Mol. Microbiol.*, 2000, 37:583-594.
Fang, M. et al., "A promoter relay mechanism for sequential gene activation," *J. Bacteriol.*, 1998, 180:626-633.
Fang, M. et al., "Suppression of *leu*-500 mutation in topA⁺ *Salmonella typhimurium* Strains, The Promoter Relay at Work," *J. Biol. Chem.*, 1998, 273:29929-29934.
Fulcrand, G. et al., "DNA supercoiling, a critical signal regulating the basal expression of the *lac* operon in *Escherichia coli*," *Sci. Rep.*, 2016, 6:19243.
Kouzine, F. et al. "Transcription-dependent dynamic supercoiling is a short-range genomic force," *Nat. Struct. Mol. Biol.*, 2013, 20:396-403.
Lacadie, S.A. et al., "Divergent Transcription and Epigenetic Directionality of Human Promoters," *FEBS J.*, 2016, 1-9.
Leng, F. et al., "Dividing a supercoiled DNA molecule into two independent topological domains," *Proc. Natl. Acad. Sci. U. S. A.*, 2011, 108:19973-19978.

(Continued)

*Primary Examiner* — Addison D Ault
(74) *Attorney, Agent, or Firm* — Saliwanchik, Lloyd & Eisenschenk

(57) ABSTRACT

The disclosure describes the effects of transcription mediated from a promoter on the transcription mediated by divergently coupled supercoiling-sensitive promoter. Transcription initiated from a promoter inhibits transcription mediated by a specific supercoiling-sensitive promoter that is divergently coupled to the promoter. A gyrase inhibitor relieves this inhibition and substantially increases the transcription mediated by the specific supercoiling-sensitive promoter that is divergently coupled to another promoter. Accordingly, the invention pertains to a method for identifying a compound as a gyrase inhibitor or not a gyrase inhibitor based on differential expression of genes under the control of divergently coupled promoters in the presence of the compound. Another embodiment of the invention provides an assay for identifying one or more compounds from a library of compounds as a gyrase inhibitor. Polynucleotides and cells containing such polynucleotides that are suitable for carrying out the methods described herein are also provided.

11 Claims, 15 Drawing Sheets

(56) References Cited

OTHER PUBLICATIONS

Leng, F. et al., "Potent stimulation of transcription-coupled DNA supercoiling by sequence-specific DNA-binding proteins," *Proc. Natl. Acad. Sci. U. S. A.*, 2002, 99:9139-9144.

Lilley, D.M. et al., "Local DNA topology and gene expression: the case of the leu-500 promoter," *Mol. Microbiol.*, 1991, Abstract only.

Liu, L.F. et al., "Supercoiling of the DNA template during transcription," *Proc. Natl. Acad. Sci. U. S. A.*, 1987, 84:7024-7027.

Ma, J. et al., "RNA polymerase is a powerful torsional motor," *Cell Cycle*, 2014, 13:337-338.

Ma, J. et al., "Transcription under torsion," *Science*, 2013, 340:1580-1583.

Marquardt, S. et al. "A chromatin-based mechanism for limiting divergent noncoding transcription," *Cell*, 2014, 157:1712-1723.

McKenzie, G.J. et al., "Fast, easy and efficient: site-specific insertion of transgenes into enterobacterial chromosomes using Tn7 without need for selection of the insertion event," *BMC. Microbiol.*, 2006, 6:39.

Menzel, R. et al., "Modulation of transcription by DNA supercoiling: a deletion analysis of the *Escherichia coli* gyrA and gyrB promoters," *Proc. Natl. Acad. Sci. U. S. A.*, 1987, 84:4185-4189.

Mielke, S.P. et al., "Transcription-driven twin supercoiling of a DNA loop: a Brownian dynamics study," *J. Chem. Phys.*, 2004, 121:8104-8112.

Miller, J. H., "Experiments in Molecular Genetics," *Cold Spring Harbor Laboratory*, 1972, Abstract only.

Mukai, F.H. et al., "Analysis of Unlinked Suppressors of an O degrees Mutation in *Salmonella*," *Proc. Natl. Acad. Sci. U. S. A.*, 1963, 50:140-148.

Naughton, C. et al. "Transcription forms and remodels supercoiling domains unfolding large-scale chromatin structures," *Nat. Struct. Mol. Biol.*, 2013:20, 387-395.

Neil, H. et al., "Widespread bidirectional promoters are the major source of cryptic transcripts in yeast," *Nature*, 2009, 457:1038-1042.

Nelson, P., "Transport of torsional stress in DNA," *Proc. Natl. Acad. Sci. U. S. A.*, 1999, 96:14342-14347.

Opel, M.L. et al., "DNA supercoiling-dependent transcriptional coupling between the divergently transcribed promoters of the ilvYC operon of *Escherichia coli* is proportional to promoter strengths and transcript lengths," *Mol. Microbiol.*, 2001, 39:191-198.

Proudfoot, N. et al.,"Gene Silencing CUTs Both Ways," *Cell*, 2007, 131:649-651.

Pruss, G.J., "DNA Topoisomerase I Mutants. Increased Heterogeneity in Linking Number and other Replicon-dependent Changes in DNA Supercoiling," *J. Mol. Biol.*, 1985, 185:51-63.

Pruss, G.J. et al., "DNA supercoiling and suppression of the leu-500 promoter mutation," *J. Bacteriol.*, 1985, 164:947-949.

Rhee, K.Y. et al., "Transcriptional coupling between the divergent promoters of a prototypic LysR-type regulatory system, the ilvYC operon of *Escherichia coli*," *Proc. Natl. Acad. Sci. U. S. A*, 1999, 96:14294-14299.

Samul, R. et al., "Transcription-coupled hypernegative supercoiling of plasmid DNA by T7 RNA polymerase in *Escherichia coli* topoisomerase I-deficient strains," *J. Mol. Biol.* 374:925-935.

Scruggs, B.S. et al. "Bidirectional Transcription Arises from Two Distinct Hubs of Transcription Factor Binding and Active Chromatin," *Mol. Cell.*, 2015, 58:1101-1112.

Seila, A.C. et al., "Divergent transcription: a new feature of active promoters," *Cell Cycle*, 2009, 8:2557-2564.

Seila, A.C. et al., "Divergent transcription from active promoters," *Science*, 2008, 322:1849-1851.

Sigova, A.A. et al., "Divergent transcription of long noncoding RNA/mRNA gene pairs in embryonic stem cells," *Proc. Natl. Acad. Sci. U. S. A.*, 2013, 110:2876-2881.

Snoep, J.L. et al., "DNA supercoiling in *Escherichia coli* is under tight and subtle homeostatic control, involving gene-expression and metabolic regulation of both topoisomerase I and DNA gyrase," *Eur. J. Biochem.*, 2002, 269:1662-1669.

Straney, R. et al., "Mutations in the −10 TATAAT sequence of the gyrA promoter affect both promoter strength and sensitivity to DNA supercoiling," *J. Bacteriol.*, 1994, 176:5999-6006.

Tan, J. et al., "Activation of the leu-500 promoter by adjacent transcription," *J. Bacteriol.*, 1994, 176:1077-1086.

Tsao, Y.P. et al., "Transcription-driven supercoiling of DNA: direct biochemical evidence from in vitro studies," *Cell*, 1989, 56:111-118.

Unniraman, S. et al., "Axial distortion as a sensor of supercoil changes: a molecular model for the homeostatic regulation of DNA gyrase," *J. Genet.*, 2001, 80:119-124.

Vera, J.M. et al., "Survey of cryptic unstable transcripts in yeast," *BMC Genomics*, 2016, 17:305.

Waddell, C.S. et al., "Tn7 transposition: recognition of the attTn7 target sequence," *Proc. Natl. Acad. Sci. U. S. A.*, 1989, 86:3958-3962.

Wu, H.Y. et al., "DNA supercoiling and transcription control: a model from the study of suppression of the leu-500 mutation in *Salmonella typhimurium* topA-strains," *Prog. Nucleic Acid Res. Mol. Biol.*, 2003, 73:43-68.

Wu, H.Y. et al., "Long-range interaction between two promoters: activation of the leu-500 promoter by a distant upstream promoter," *Cell*, 1995, 82:445-451.

Wu, H.Y. et al., "Transcription generates positively and negatively supercoiled domains in the template," *Cell*, 1988, 53, 433-440.

Xu, Z. et al. "Bidirectional promoters generate pervasive transcription in yeast," *Nature*, 2009, 457:1033-1037.

Yamada, M. et al., "Divergent promoter organization may be a preferred structure for gene control in *Escherichia coli*," *J. Mol. Microbiol. Biotechnol.*, Abstract only.

Zechiedrich, E.L. et al., "Roles of topoisomerases in maintaining steady-state DNA supercoiling in *Escherichia coli*," *J. Biol. Chem.*, 2000, 275:8103-8113.

Zhi, X. et al., "Dependence of transcription-coupled DNA supercoiling on promoter strength in *Escherichia coli* topoisomerase I deficient strains," *Gene*, 2013, 514:82-90.

\* cited by examiner

```
TTAGTGGCACTGGATATGCCGTTTAATGTCAACTCTATTTTC
   -10              P_leu-500          -35
TGGGATCCCAAATAGGGGTTCCGCGCACATTTCCCCGAAA AGTGCCACCTGACGTGAATTCAAAAAGAGTATTGACTTGTG
                                        -35
AGCGGATAACAATGATACTTACA
 P_T7A1/O4       -10
```

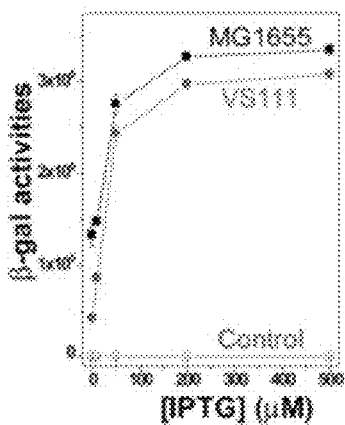
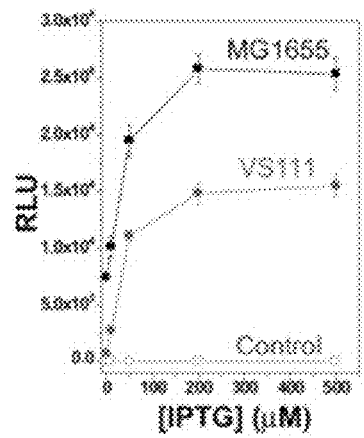
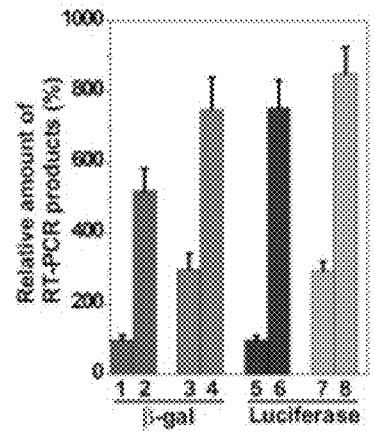
FIG. 2A
FIG. 2B
FIG. 2C
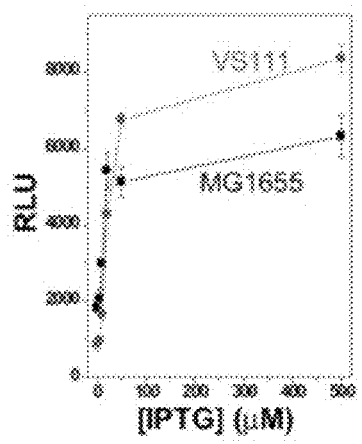
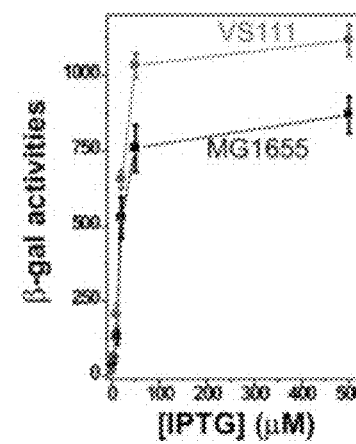
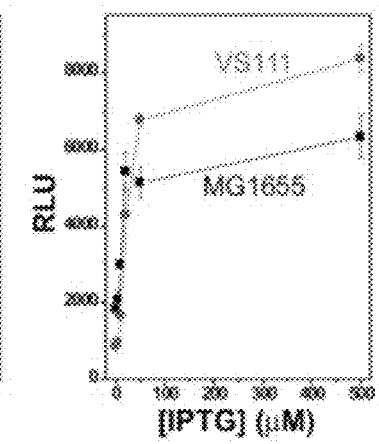
FIG. 2D
FIG. 2E
FIG. 2F

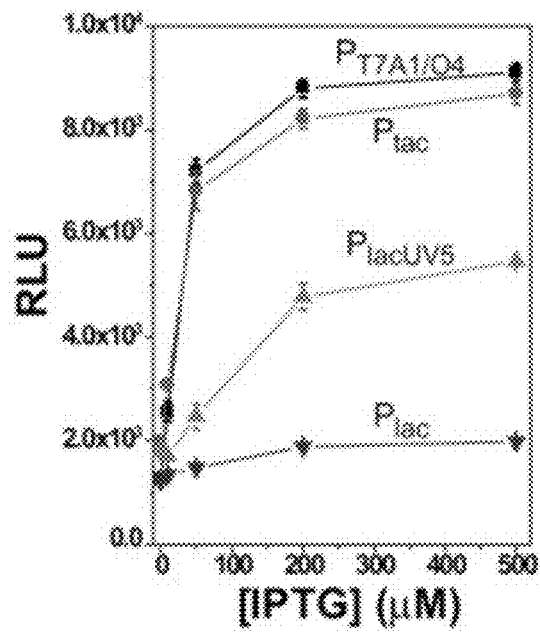
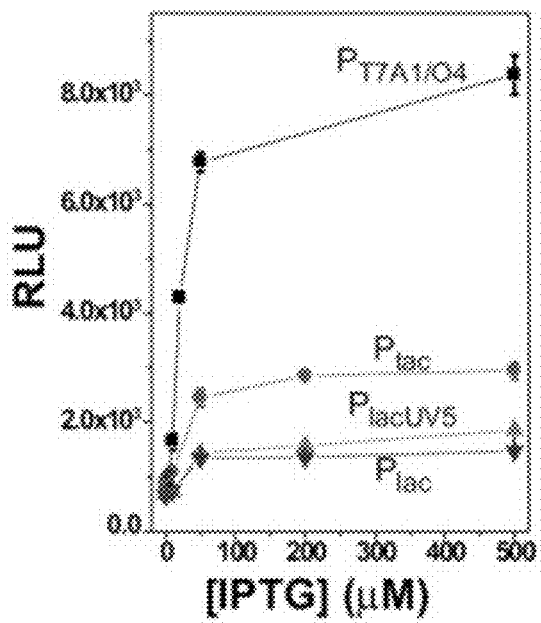
FIG. 3A
FIG. 3B
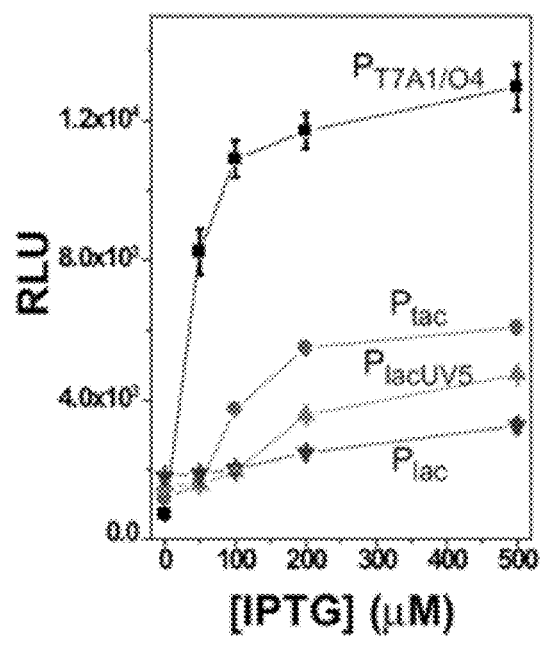
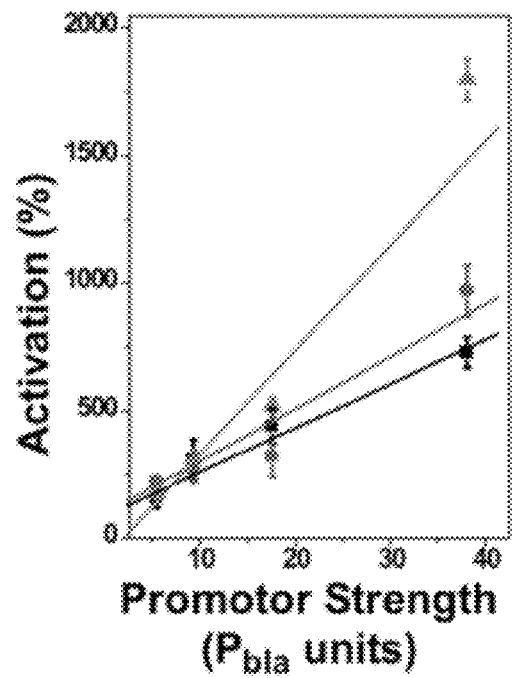
FIG. 3C
FIG. 3D

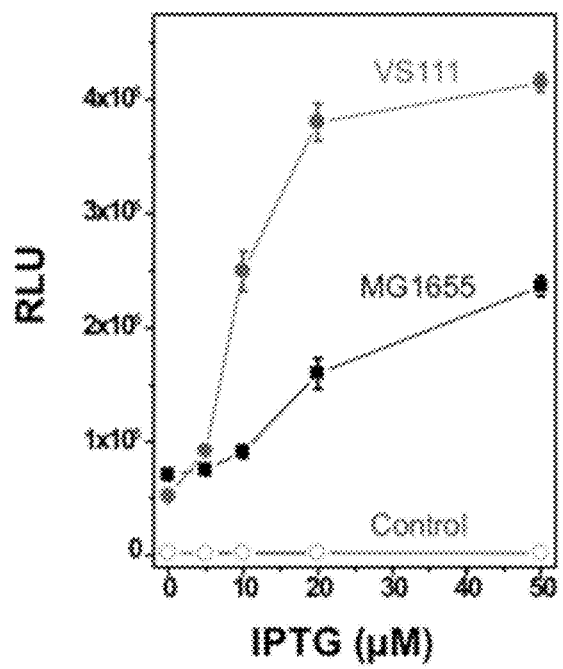 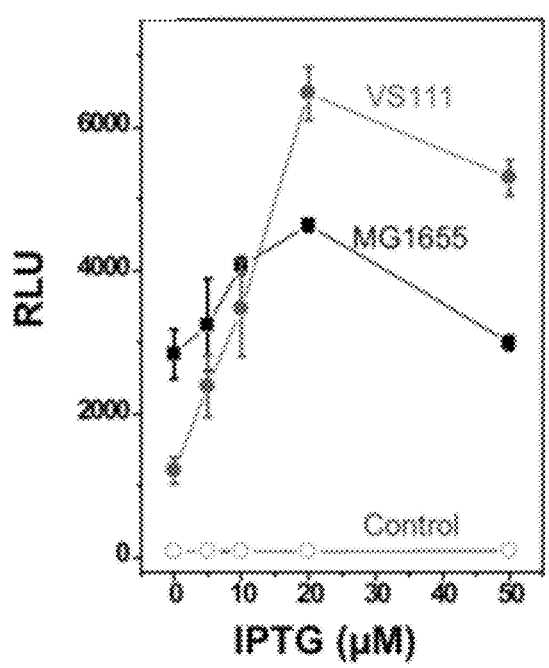
FIG. 4A    FIG. 4B
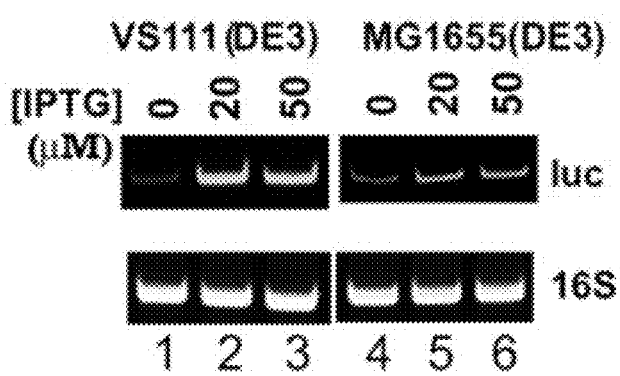 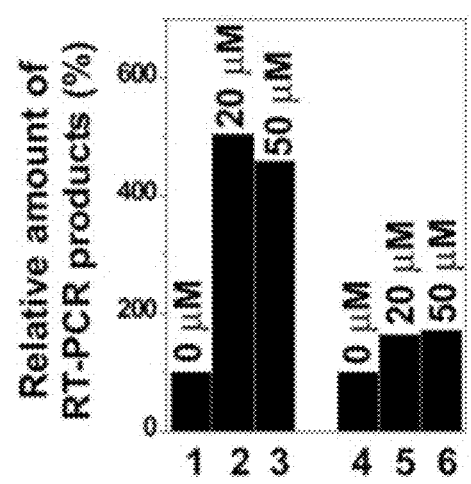
FIG. 4C    FIG. 4D

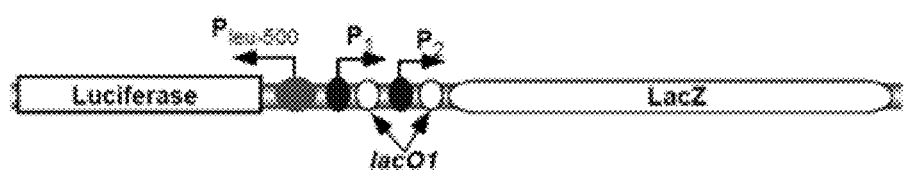
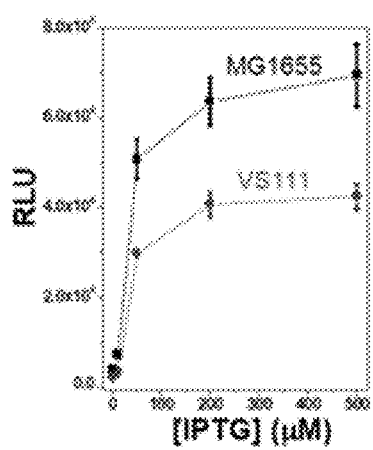 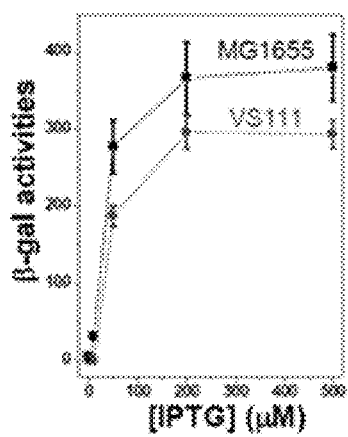 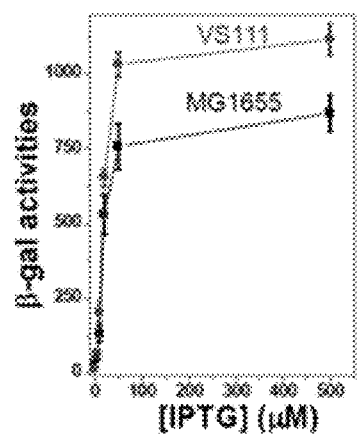
FIG. 7A          FIG. 7B          FIG. 7C

```
AAATTATAACACAGCCGCGCAGTTTGAGGTAAACCTATACGCTTT
   -10          P_gyrA           -35
ATTCACATCCGGATCCCAAATAGGGGTTCCGCGCACATTTCCCC GAAAAGTGCCACCTGACGTGAATTCAAAAAGAGTATTGACTTGT
                                        -35

GAGCGGATAACAATGATACTTA
 P_T7A1/O4    -10
```

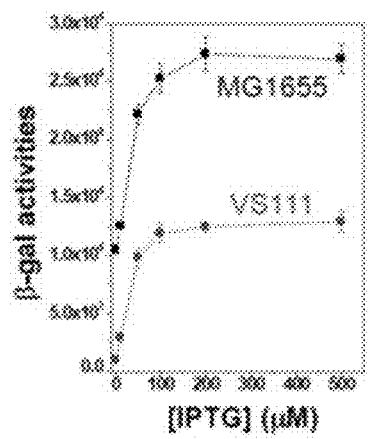
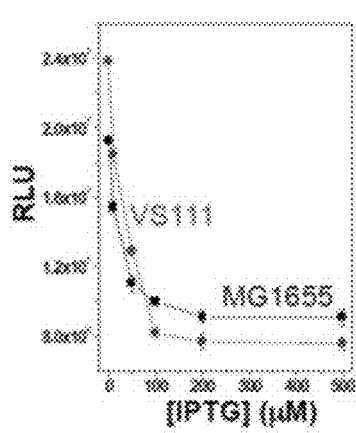
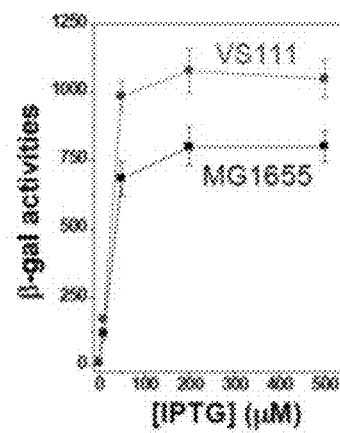
FIG. 12A  FIG. 12B  FIG. 12C
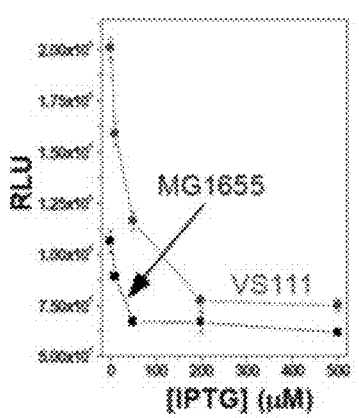
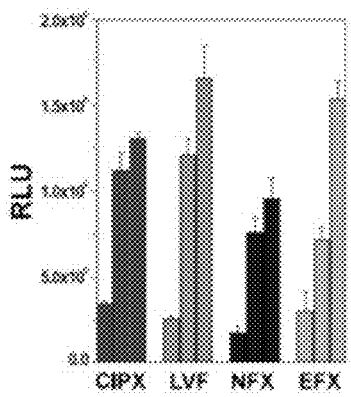
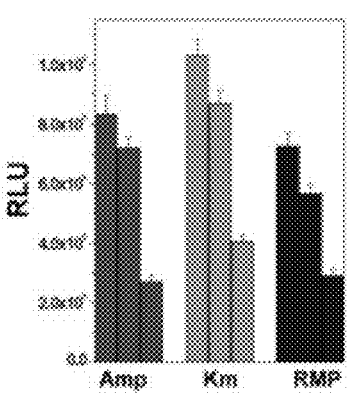
FIG. 12D  FIG. 12E  FIG. 12F
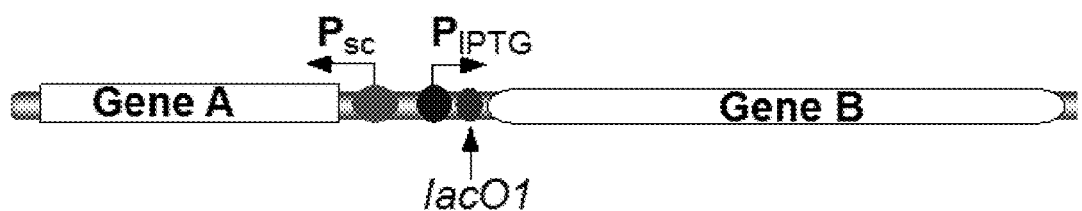
FIG. 13A

MATERIALS AND METHODS FOR IDENTIFYING GYRASE INHIBITORS

The Sequence Listing for this application is labeled "SeqList-01Sep16.txt," which was created on Sep. 1, 2016, and is 4 KB. The entire content is incorporated herein by reference in its entirety.

BACKGROUND OF THE INVENTION

Divergently coupled transcription or divergent transcription in which two neighboring promoters initiate transcription in opposite directions widely exists in many organisms from bacteria to humans. For instance, in murine and human cells, high throughput sequencing data showed that short noncoding RNAs (ncRNA) are always produced divergently from active promoters that direct transcription initiation of mRNA. Similarly, deep sequencing experiments and yeast whole genome tiling arrays demonstrated that a majority of yeast cryptic unstable transcripts (CUTs) are generated divergently from the promoter of functional genes.

Divergent transcription typically originates from two distinct promoters or transcription preinitiation complexes (PICs). These sense and upstream antisense transcripts arise from nucleosome depletion regions that contain two distinct hubs of transcription factor binding sites. In bacteria, many promoters are divergently coupled. For example, in the ilvYC operon of *E. coli*, the ilvY promoter is divergently coupled to the ilvC promoter. Transcriptional activities of the ilvY and ilvC promoters depend on the localized superhelical density around the promoter region. Another well-characterized example is the activation of *S. typhimurium* leu-500 promoter ($P_{leu-500}$) by divergently coupled transcription.

BRIEF SUMMARY OF THE INVENTION

The subject invention provides materials and methods for transcription regulation via divergently coupled promoters and its use in preparation of a cell, a polynucleotide and an assay for identifying gyrase inhibitors.

The effects of transcription initiated from a promoter, for example, an Isopropyl β-D-1-thiogalactopyranoside (IPTG)-inducible promoter, on the transcription mediated by divergently coupled supercoiling-sensitive promoter, for example, $P_{leu-500}$ and $P_{gyrA}$ are described. For example, transcription initiated from an IPTG-inducible promoter activates $P_{leu-500}$ and inhibit $P_{gyrA}$ or $P_{gyrB}$ mediated transcription. Gyrase inhibitors, such as ciprofloxacin, substantially increased the expression of the firefly luciferase under the control of the $P_{gyrA}$ in the presence of IPTG for *E. coli* strains that carries the divergently coupled $P_{gyrA}$ and $P_{T7A1/O4}$.

Accordingly, an embodiment of the invention provides a method for identifying a compound as a gyrase inhibitor or not a gyrase inhibitor, the method comprising the steps of:
a) providing a cell or a culture of the cell, wherein the cell comprises a polynucleotide comprising:
   i) a first promoter operably linked to a first gene, and
   ii) a second promoter operably linked to a second gene, wherein the second promoter is divergently coupled to the first promoter, and
   wherein the transcription of the operably linked second gene under the control of
   the second promoter is inhibited by negative supercoiling of the second promoter;
b) optionally, culturing the cell or the culture of the cell;
c) incubating a first portion of the culture, provided in step a) or cultured in step b), in the presence of the compound and incubating a second portion of the culture, provided in step a) or cultured in step b), in the absence of the compound;
d) measuring the expression of the first gene and/or the second gene in the first portion and/or the second portion after the incubation of step c); and
e) identifying the compound as:
   i) the gyrase inhibitor, if the expression of the second gene is higher in the first portion compared to the expression of the second gene in the second portion, or
   i) not the gyrase inhibitor, if the expression of the second gene is not higher in the first portion compared to the expression of the second gene in the second portion.

Another embodiment of the invention provides an assay for identifying one or more compounds from a library of compounds as a gyrase inhibitor. A gyrase inhibitor identified according to the methods described herein can be used as an inhibitor of a cell, for example, a bacterial cell used in the assay.

Further embodiments of the invention provide a polynucleotide comprising:
   i) a first promoter operably linked to a first gene, and
   ii) a second promoter operably linked to a second gene, wherein the second promoter is divergently coupled to the first promoter, and wherein the transcription of the operably linked second gene under the control of the second promoter is inhibited by negative supercoiling of the second promoter. A cell containing the polynucleotide described herein is also provided.

BRIEF DESCRIPTION OF THE FIGURES

(FIG. 1A) Divergently coupled promoters $P_{T7A1/O4}$ and $P_{leu-500}$ were used to control the expression of β-galactosidase (lacZ) and firefly luciferase (luc), respectively. (FIG. 1B) The DNA sequence of the divergently coupled promoters, $P_{T7A1/O4}$ and $P_{leu-500}$ (SEQ ID NO: 1). (FIG. 1C) and (FIG. 1D) Maps of circular plasmid pZXD133 and linear plasmid pZXD143. Winged triangles represent a set of 4 Rho-independent *E. coli* rrnB T1 terminators. The directions of the T7 promoter, the leu-500 promoter, luc, lacZ, and T1 terminators are indicated.

FIGS. 2A-2F. Activation of the supercoiling-sensitive $P_{leu-500}$ by *E. coli* RNA polymerase. Activities of β-galactosidase and firefly luciferase were measured as described under Materials and Methods. Briefly, overnight cultures of *E. coli* cells were diluted 100-fold and grown in the presence of various amounts of IPTG to an OD600 of 0.5, and assayed for β-galactosidase (Miller's units) and luciferase activities (Raw light units (RLU)). (FIG. 2A) and (FIG. 2B) Activities of β-galactosidase and firefly luciferase for MG1655(DE3) ΔlacZ (black squares) and VS111(DE3) ΔlacZ (solid circles) that carry circular plasmid pZXD133. Open circles represent results from VS111(DE3) ΔlacZ carrying the circular plasmid pZXD95 that does not contain a $P_{T7A1/O4}$ as controls. (FIG. 2C) Real-time RT-PCR analyses for VS111(DE3) ΔlacZ (columns 1, 2, 5, and 6) or MG1655(DE3) ΔlacZ (columns 3, 4, 7, and 8) carrying pZXD133. (FIG. 2D) Activities of firefly luciferase for MG1655(DE3) ΔlacZ (black squares) and VS111(DE3) ΔlacZ (solid circles) that carry linear plasmid pZXD143. (FIG. 2E) and (FIG. 2F) The activation of $P_{leu-500}$ by *E. coli* RNA polymerase on the chromosome for FL1130 (MG1655 (DE3)ΔlacZ attTn7::

$P_{T7A1/O4}$lacZ-$P_{leu-500}$luc; black squares) and FL1131 (VS111(DE3)ΔlacZ attTn7::$P_{T7A1/O4}$lacZ-$P_{leu-500}$luc; solid circles).

FIGS. 3A-3D. Activation of $P_{leu-500}$ by E. coli RNA polymerase in E. coli topA strain VS111(DE3) ΔlacZ is dependent on the promoter strength at circular plasmid (FIG. 3A), linear plasmid (FIG. 3B), and chromosomal (FIG. 3C) levels. (FIG. 3D) The activation level in the presence of 500 μM of IPTG. Squares, circles, and triangles represent the activation for circular plasmids, linear plasmids, and chromosomes.

FIGS. 4A-4D. Activation of $P_{leu-500}$ by T7 RNA polymerase. (FIG. 4A) and (FIG. 4B) Luciferase activities were measured as described under Materials and Methods. E. coli topA strain VS111(DE3) (open circles) and wild-type strain MG1655 (DE3) (solid circles) carrying the circular plasmid pZXD99 (FIG. 4A) or the linear plasmid pZXD103 (FIG. 4B). (FIG. 4C) RT-PCR assays and (FIG. 4D) Real-time RT-PCR analyses for VS111(DE3) or MG1655(DE3) carrying pZXD99.

FIGS. 5A-5D. (FIG. 5A) and (FIG. 5B) Inhibition of the supercoiling-sensitive $P_{gyrA}$ by E. coli RNA polymerase on the chromosome. E. coli strains FL1181 (MG1655(DE3) ΔlacZ attTn7::$P_{T7A1/O4}$lacZ-$P_{gyrA}$luc; squares) and FL1182 (VS111(DE3)ΔlacZ attTn7::$P_{T7A1/O4}$lacZ-$P_{gyrA}$luc; circles) were used. The activities of β-galactosidase (Miller's units) and firefly luciferase (RLU) were plotted against the IPTG concentration added to the cell cultures. (FIG. 5C) and (FIG. 5D) DNA gyrase inhibitors significantly enhanced the expression of firefly luciferase for FL1181 and FL1182 in the presence of IPTG. Overnight cell cultures were diluted 100-fold and grown until OD600 reached 0.2. Then 0.5 mM of IPTG and various concentrations of ciprofloxacin or other antibiotics were added to the cell cultures. After additional 30 min incubation, the activities of β-galactosidase and firefly luciferase were measured as described under Materials and Methods. (FIG. 5C) Ciprofloxacin inhibited the expression of β-galactosidase. (FIG. 5D) Ciprofloxacin greatly enhanced the expression of firefly luciferase.

Figure 6:
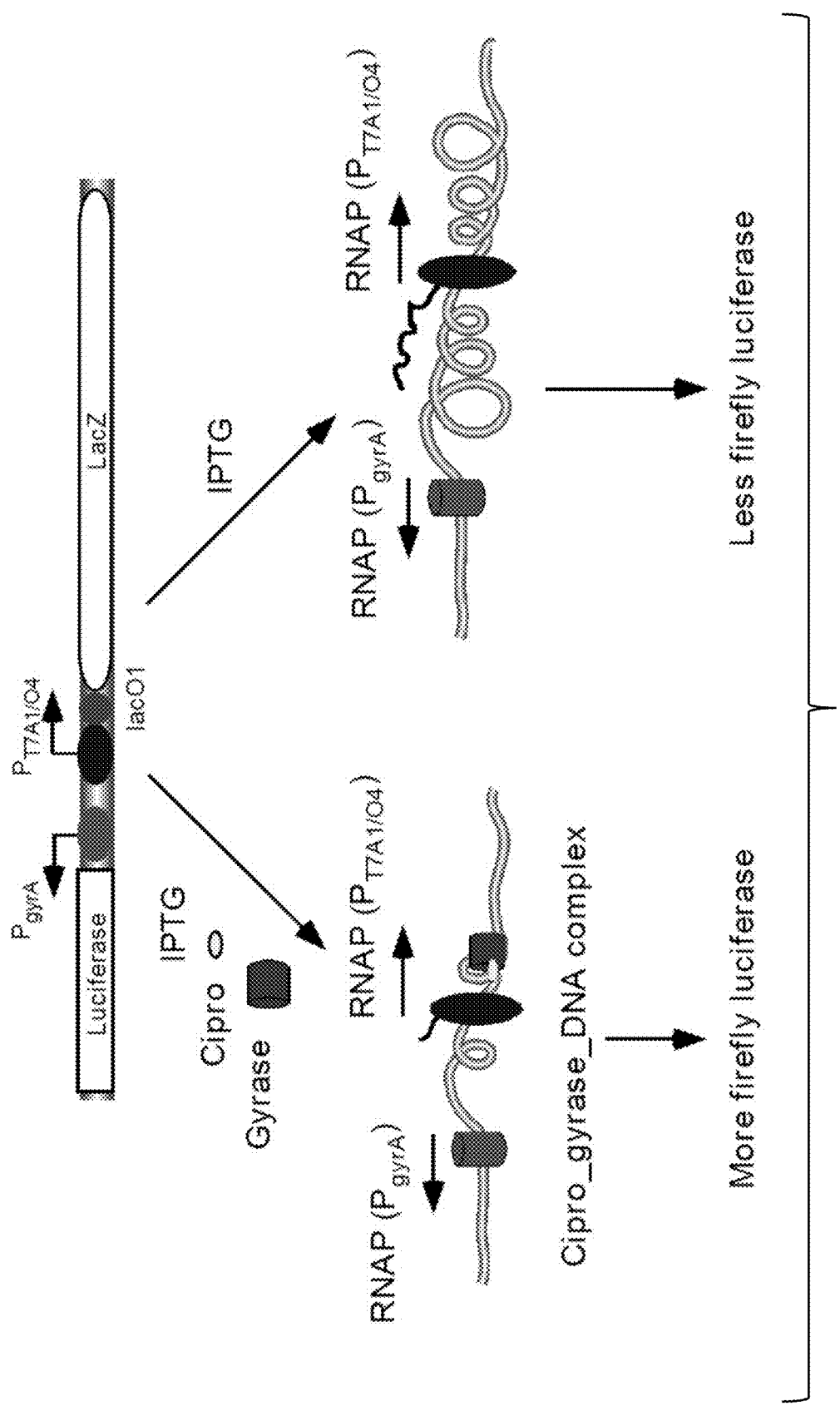

FIG. 6. TCDS can be used to screen DNA gyrase inhibitors. In the presence of IPTG (right panel), transcription from $P_{T7A1/O4}$ induces significant TCDS and inhibits the expression of firefly luciferase from $P_{gyrA}$. However, in the presence of gyrase inhibitor ciprofloxacin, ciprofloxacin stabilizes gyrase-cipro-DNA complex that blocks transcription from $P_{T7A1/O4}$. The (−) supercoils behind RNA polymerase are not formed. As a result, the expression of firefly luciferase is "enhanced."

FIGS. 7A-7C. Activation of the supercoiling-sensitive $P_{leu-500}$ by E. coli RNA polymerase for IPTG-inducible ribosomal rrnB P1 and P2 promoters. Activities of β-galactosidase and firefly luciferase were measured as described under Materials and Methods. (FIG. 7A) The activities of β-galactosidase (miller's units) for MG1655(DE3)ΔlacZ (squares) and VS111(DE3)ΔlacZ (solid circles) that carry linear plasmid pZXD143. (FIG. 7B) and (FIG. 7C) E. coli strains FL1261 (MG1655(DE3)ΔlacZ attTn7::rrnB$P_1$, $P_{2/lacO1}$lacZ-$P_{leu-500}$luc; squares) and FL1262 (VS111(DE3) ΔlacZ attTn7::rrnB$P_1$,$P_{2/lacO1}$lacZ-$P_{leu-500}$luc; circles) were used. The activities of β-galactosidase (miller's units) and firefly luciferase (RLU) were plotted against the IPTG concentration added to the cell cultures.

Figure 8:
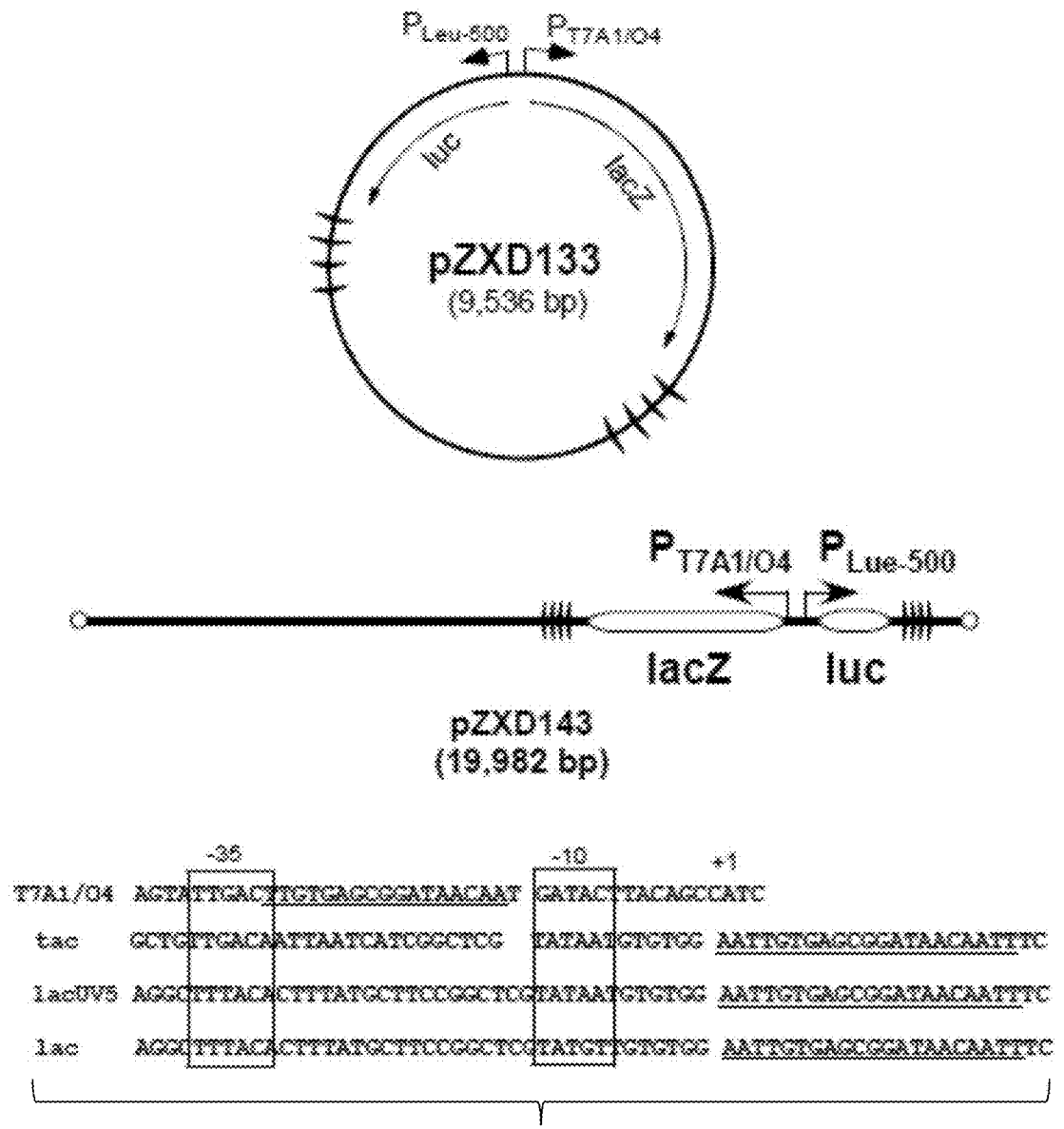
Figure 9A:
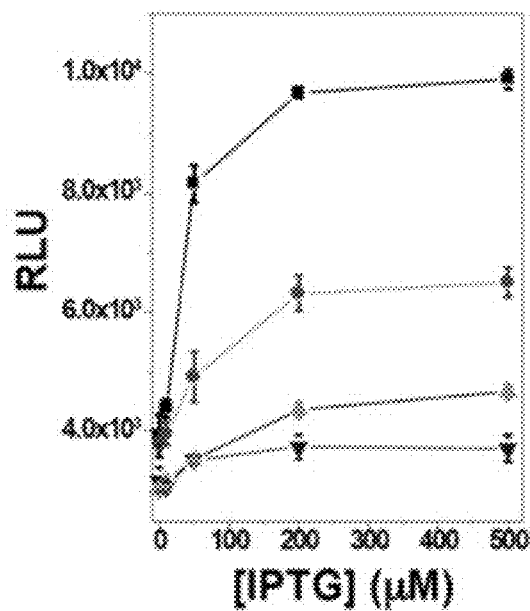
Figure 9B:
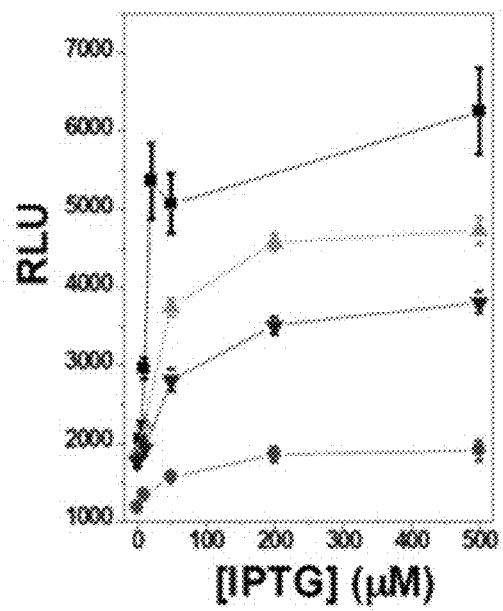
Figure 9C:
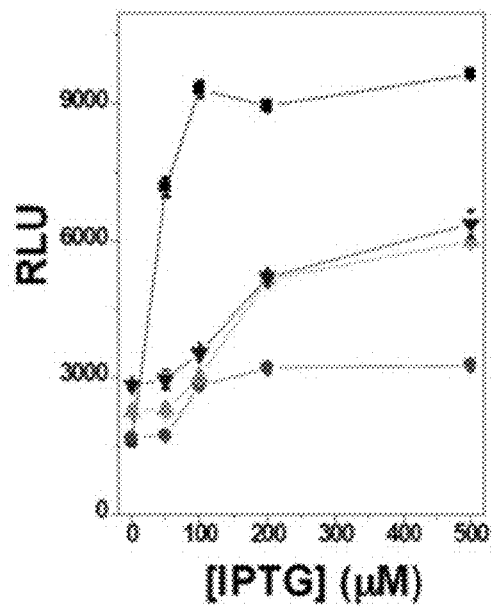
Figure 9D:
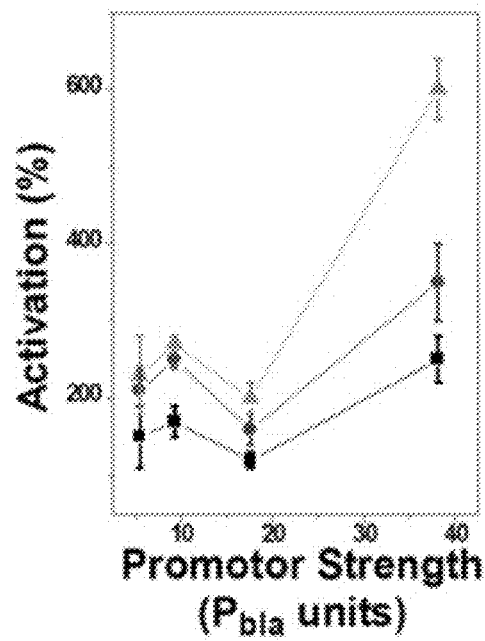

FIG. 8. Circular and linear plasmid carrying IPTG-inducible promoters with different strength. The DNA sequence of four different E. coli promoters $P_{T7A1/O4}$ (SEQ ID NO: 2), $P_{tac}$ (SEQ ID NO: 3), $P_{lacUV5}$ (SEQ ID NO: 4), and $P_{lac}$ (SEQ ID NO: 5). The underlines represent the lac O1 operators.

FIGS. 9A-9D. Activation of $P_{leu-500}$ by E. coli RNA polymerase in E. coli wild-type strain MG1655(DE3) ΔlacZ is dependent on the promoter strength at circular plasmid (FIG. 9A), linear plasmid (FIG. 9B), and chromosomal (FIG. 9C) levels. (FIG. 9D) The activation level in the presence of 500 μM of IPTG. Squares, circles, and triangles represent the activation for circular plasmids, linear plasmids, and chromosomes.

Figure 10:
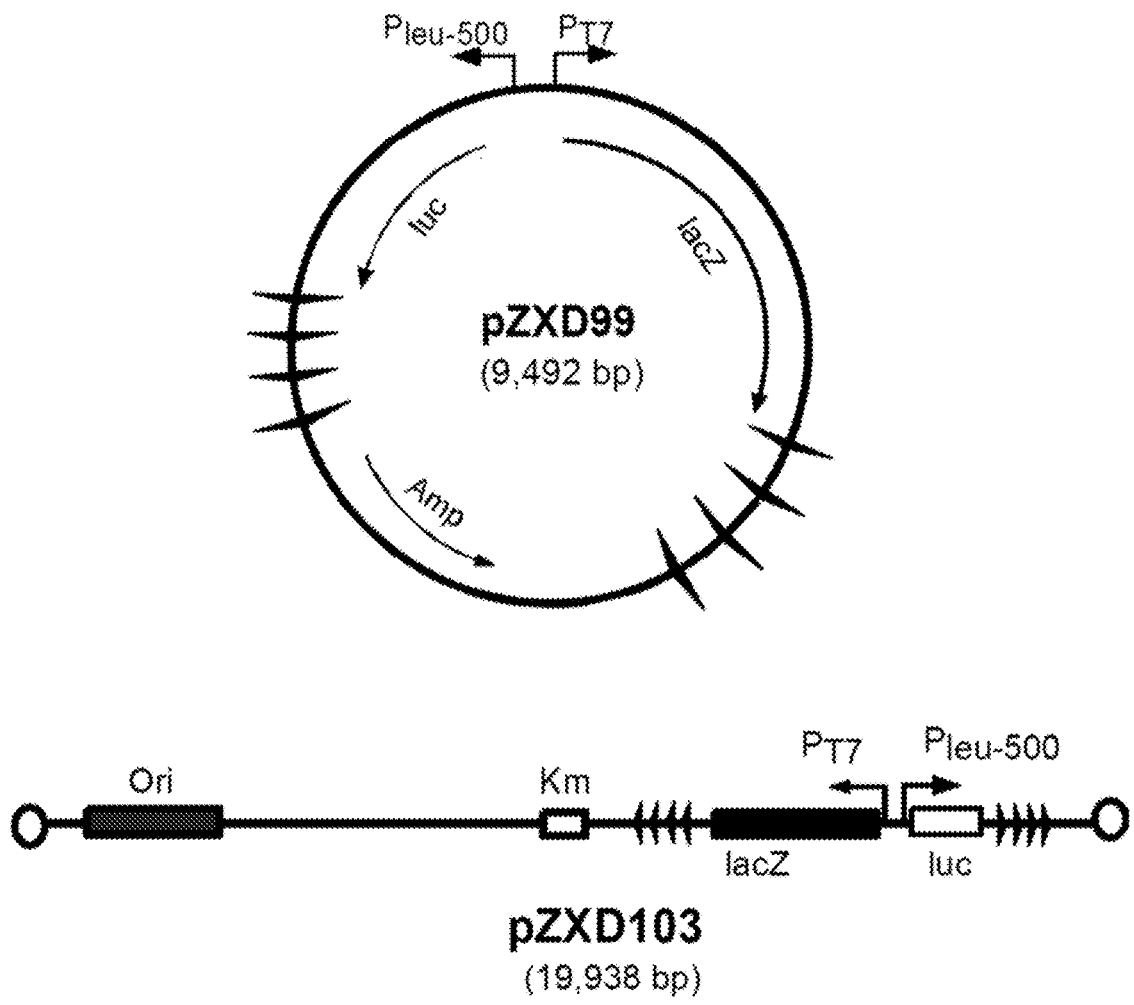

FIG. 10. Maps of plasmids pZXD99 and pZXD103, each of which carries a T7 promoter. Plasmid pZXD99 was derived from pBR322. The linear plasmid pZXD103 was derived from the linear coliphage N15-based plasmid pG591. $P_{leu-500}$ and $P_{T7}$ represent the leu-500 and the T7 promoter, respectively. These two promoters are divergently coupled. Luc is the firefly luciferase gene. Winged triangles represent a set of 4 Rho-independent E. coli rrnB T1 terminators. The directions of the T7 promoter, the leu-500 promoter, luc, lacZ, and T1 terminators are indicated.

FIGS. 11A-11D. Design of divergently coupled transcription to study transcription inhibition of $P_{gyrA}$ in E. coli. (FIG. 11A) Divergently coupled promoters $P_{T7A1/O4}$ and $P_{gyrA}$ (SEQ ID NO: 6) were used to control the expression of β-galactosidase (lacZ) and firefly luciferase, respectively. (FIG. 11B) The DNA sequence of the divergently coupled promoters, $P_{T7A1/O4}$ and $P_{gyrA}$. (FIG. 11C) and (FIG. 11D) Maps of circular plasmid pZXD144 and linear plasmid pZXD150. Winged triangles represent a set of 4 Rho-independent E. coli rrnB T1 terminators. The directions of the T7 promoter, the leu-500 promoter, luc, lacZ, and T1 terminators are indicated.

FIGS. 12A-12F. (FIG. 12A) and (FIG. 12B) Inhibition of the supercoiling-sensitive $P_{gyrA}$ by E. coli RNA polymerase for circular plasmid pZXD144. E. coli strains MG1655 (DE3)ΔlacZ (squares) and VS111(DE3)ΔlacZ (circles) carrying pZXD144 were used. The activities of β-galactosidase (miller's units) and firefly luciferase (RLU) were plotted against the IPTG concentration added to the cell cultures. (FIG. 12C) and (FIG. 12D) Inhibition of the supercoiling-sensitive $P_{gyrA}$ by E. coli RNA polymerase for lineasr plasmid pZXD150. E. coli strains MG1655(DE3)ΔlacZ (squares) and VS111(DE3)ΔlacZ (circles) carrying pZXD150 were used. The activities of β-galactosidase (miller's units) and firefly luciferase (RLU) were plotted against the IPTG concentration added to the cell cultures. (FIG. 12E) The stimulation of expression of firefly luciferase of FL#1181 by other gyrase inhibitors in the presence of IPTG. Cipro, Levo, Enro, and Nor represent ciprofloxacin, levofloxacin, enrofloxacin, and norfloxacin, respectively. (FIG. 12F) The inhibition of expression of firefly luciferase by other antibiotics. Rif, Spc, Amp, and Tc represent rifampicin, spectinomycin, ampicillin, and tetracycline, respectively.

FIGS. 13A-13E. General strategy to design plasmids and E. coli strains to target TCDS for the identification of new antibiotics against bacterial DNA gyrase. $P_{sc}$, supercoiling sensitive promoter; $P_{IPTG}$, IPTG inducible promoter; lacZ, E. coli lacZ gene; luc, the firefly luciferase gene; YFP, the yellow fluorescence protein gene; lacO1, the lac O1 operator.

BRIEF DESCRIPTION OF SEQUENCES

SEQ ID NO: 1: Sequence of a divergently coupled $P_{leu-500}$ with $P_{T7A1/O4}$ promoter,
SEQ ID NO: 2: The sequence of E. coli promoter T7A1/O4.
SEQ ID NO: 3: The sequence of E. coli promoter tac.
SEQ ID NO: 4: The sequence of E. coli promoter lacUV5.
SEQ ID NO: 5: The sequence of E. coli promoter lac.
SEQ ID NO: 6: Sequence of a divergently coupled $P_{gyrA}$ with $P_{T7A1/O4}$ promoter.

SEQ ID NO: 7: Sequence of forward primer for amplification of luc gene.
SEQ ID NO: 8: Sequence of reverse primer for amplification of luc gene.
SEQ ID NO: 9: Sequence of forward primer for amplification of 16s rRNA gene.
SEQ ID NO: 10: Sequence of reverse primer for amplification of 16s rRNA gene.
SEQ ID NO: 11: Sequence of forward primer for amplification of lacZ gene.
SEQ ID NO: 12: Sequence of reverse primer for amplification of lacZ gene.
SEQ ID NO: 13: The sequence of the $P_{gyrB}$ promoter.

DETAILED DESCRIPTION OF THE INVENTION

A gyrase inhibitor refers to a compound that inhibits the activity of gyrase. Gyrase is an enzyme that introduces (−) supercoils into DNA substrates in a reaction that requires the hydrolysis of ATP. Gyrase is also known as DNA topoisomerase II. Relieving strain while double-strand DNA is being overwound by DNA replication or transcription causes negative supercoiling of the DNA. Certain aspects of the mechanism of DNA supercoiling by DNA gyrase are described in the Collin et al. reference, the contents of which are herein incorporated by reference in its entirety, particularly, page 480, under "Mechanism of DNA supercoiling by DNA gyrase" and FIG. 1.

A gyrase inhibitor can inhibit the enzymatic activity of gyrase or stabilize the covalent enzyme-DNA complex. Certain aspects of the gyrase inhibitors are described in the Collin et al. (2010) reference, the contents of which are herein incorporated by reference in its entirety, particularly, pages 480-492, under "Catalytic inhibitors of gyrase vs. gyrase poisons" and FIGS. 2-7.

A compound that is not a gyrase inhibitor does not inhibit the activity of gyrase.

A cell as used herein can be a prokaryotic or eukaryotic cell. Non-limiting examples of a cell include a bacterial, fungal, plant, algal, protozoan, or animal cell. An animal cell can be a mammalian or insect cell. A fungal cell can be a filamentous fungal cell or yeast cell.

A culture of a cell refers to a group of cells obtained by growing a cell in a culture medium under appropriate conditions. Therefore, a culture typically comprises a clonal population of cells.

A polynucleotide as used herein refers to a double-stranded DNA, a single-stranded DNA, or products of transcription of the said DNAs, e.g., RNA. The polynucleotide nucleotide of the invention can be isolated, purified, or partially purified by separation methods, for example, ion-exchange chromatography, molecular size exclusion chromatography, or by genetic engineering methods such as amplification, subtractive hybridization, cloning, subcloning or chemical synthesis, or combinations of these methods.

As used herein, the phrase "a promoter operably linked to a gene" indicates that the promoter induces transcription of the gene. A promoter can be a constitutive promoter that induces the transcription of an operably linked gene without the need for an inducer of transcription. A promoter can also be an inducible promoter. An inducible promoter requires the presence of an inducer to induce the expression of an operably linked gene. An inducer is an agent, for example, a small molecule compound, that facilitates a promoter mediated induction of an operably linked gene. In a promoter operably linked to a gene, the coding sequence of the gene remains in the proper reading frame with respect to the promoter. In this manner, the nucleotide sequences for the promoters are provided in DNA constructs along with an operably linked gene for expression in a cell.

Additionally, a promoter can be operably linked to a heterologous gene. A heterologous gene is a gene which is not present under the control of a promoter in nature. A heterologous gene can be from the same organisms; however, the location of the heterologous gene in the genome of a cell according to the invention can be different from a naturally occurring cell.

A gene is a DNA sequence that can be transcribed into an mRNA by an RNA polymerase. A gene can encode an mRNA that can be translated to a full length functional protein, a fragment of a protein, or a small peptide containing about five to twenty amino acids. A gene can also encode an untranslatable mRNA, which is an mRNA that cannot be processed by the translation machinery to produce a peptide. Accordingly, a gene can contain a few, several hundred, or one or more kilobases of nucleotides.

Figures 1A, 1B:
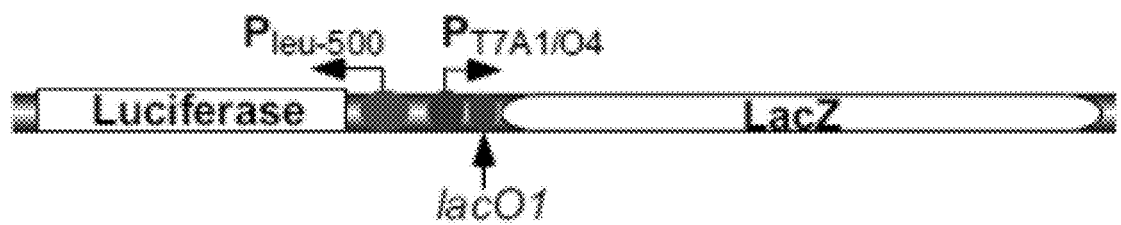
FIGS. 1A-1D. Design of divergently coupled transcription to study transcription activation of $P_{leu-500}$ in *E. coli*.

A second promoter "divergently coupled" to a first promoter indicates that first and the second promoters are located on a polynucleotide in a manner that the two promoters initiate transcription in opposite directions to each other, i.e., the first promoter initiates transcription of a first gene located away from the second promoter, and the second promoter initiates transcription of a second gene located away from the first promoter. Therefore, the first promoter is located between the second promoter and the first gene on a polynucleotide; whereas, the second promoter is located between the first promoter and the second gene on a polynucleotide. An example of "divergently coupled" promoters is shown in FIG. 1 where promoters $P_{leu-500}$ and $P_{T1A1/O4}$ are divergently coupled to each other.

Supercoiling of DNA describes DNA topology, i.e., the presence and/or the extent of twists and writhes in a piece of DNA. Supercoiling can be represented mathematically by the sum of twist and writhe. The twist is the number of helical turns in the DNA and the writhe is the number of times the double helix crosses over on itself. Extra helical twists are positive and lead to positive supercoiling, while subtractive twisting causes negative supercoiling. Therefore, as used herein, the term "negative supercoiling" indicates that the DNA molecule has either a one-start left-handed helix on protein torus (the toroid) or a two-start right-handed helix with terminal loops (the plectoneme).

Typically, negative supercoils favor local unwinding of the DNA and allow transcription, DNA replication, and recombination. For certain promoters, for example, $P_{leu-500}$ or $P_{topA}$ promoter, transcription of an operably linked gene is activated by negative supercoiling of the promoter; whereas, for certain other promoters, for example, $P_{gyrA}$ or $P_{gyrB}$ promoter, transcription of an operably linked gene is inhibited by negative supercoiling of the promoter.

The subject invention provides materials and methods for transcription regulation via divergently coupled promoters and its use in preparation of a cell, a polynucleotide and an assay for identifying gyrase inhibitors.

The effects of transcription initiated from a promoter, for example, an Isopropyl β-D-1-thiogalactopyranoside (IPTG)-inducible promoter, on the transcription mediated by divergently coupled supercoiling-sensitive promoter, for example, $P_{leu-500}$ and $P_{gyrA}$ are described. For example, transcription initiated from an IPTG-inducible promoter activates $P_{leu-500}$ and inhibit $P_{gyrA}$ mediated transcription. Gyrase inhibitors, such as ciprofloxacin, substantially increased the expression of the firefly luciferase under the control of the $P_{gyrA}$ in the presence of IPTG for *E. coli* strains that carries the divergently coupled $P_{gyrA}$ and $P_{T7A1/O4}$.

This disclosure describes the effects of transcription initiated from a promoter, for example, an IPTG-inducible promoter, on the transcription mediated by divergently coupled supercoiling-sensitive promoter, for example, $P_{leu-500}$ and $P_{gyrA}$. Transcription initiated from an IPTG-inducible promoter activates $P_{leu-500}$ and inhibits $P_{gyrA}$ mediated transcription. Transient and dynamic TCDS may be responsible for this activation and inhibition. Additionally, gyrase inhibitors, such as ciprofloxacin, substantially increased the expression of the firefly luciferase under the control of the $P_{gyrA}$ in the presence of IPTG for *E. coli* strains that carries the divergently coupled $P_{gyrA}$ and $P_{T7A1/O4}$. lacZ (to express β-galactosidase) and luc (to express firefly luciferase) were placed under the control of $P_{T7A1/O4}$ and $P_{leu-500}$ or $P_{gyrA}$, respectively. $P_{T7A1/O4}$ activated $P_{leu-500}$ mediated expression and inhibited $P_{gyrA}$ mediated expression in circular plasmid, linear plasmid, and chromosomal levels. For example, at the chromosomal level, $P_{T7A1/O4}$ activated $P_{leu-500}$ mediated expression by about 18-fold and 6-fold in VS111 and MG1655 strains, respectively. Also, the extent of divergent transcription via $P_{leu-500}$ depended on the promoter strength of the divergently coupled promoter. Additionally, gyrase inhibitors, such as ciprofloxacin, substantially increased the expression of the firefly luciferase under the control of the $P_{gyrA}$ in the presence of IPTG for *E. coli* strains that carries the divergently coupled $P_{gyrA}$ and $P_{17A1/O4}$. This unique property of TCDS can be effectively used to identify antimicrobial compounds targeting bacterial DNA gyrase.

Accordingly, one embodiment of the invention provides a method for identifying a compound as a gyrase inhibitor or not a gyrase inhibitor. The method comprises the steps of:

a) providing a cell or a culture of the cell, wherein the cell comprises a polynucleotide comprising:
 i) a first promoter operably linked to a first gene, and
 ii) a second promoter operably linked to a second gene,
 wherein the second promoter is divergently coupled to the first promoter, and wherein the transcription of the operably linked second gene under the control of the second promoter is inhibited by negative supercoiling of the second promoter;

b) optionally, culturing the cell or the culture of the cell;

c) incubating a first portion of the culture, provided in step a) or cultured in step b), in the presence of the compound and incubating a second portion of the culture, provided in step a) or cultured in step b), in the absence of the compound;

d) measuring the expression of the first gene and/or the second gene in the first portion and/or the second portion after the incubation of step c); and e) identifying the compound as:
 i) the gyrase inhibitor, if the expression of the second gene is higher in the first portion compared to the expression of the second gene in the second portion, or
 i) not the gyrase inhibitor, if the expression of the second gene is not higher in the first portion compared to the expression of the second gene in the second portion.

In one embodiment, a cell is provided which can be cultured in an appropriate medium under appropriate conditions to produce a culture of cells. Alternately, a culture of cells is provided.

A cell can be a prokaryotic or eukaryotic cell. Non-limiting examples of a cell include a bacterial, fungal, plant, algal, protozoan, or animal cell. An animal cell can be, for example, a mammalian or insect cell. A fungal cell can be a filamentous fungal cell or yeast cell. In one embodiment, the cell is a bacterial cell, particularly, a pathogenic bacterial cell.

The cell used in the methods provided herein comprises a polynucleotide comprising:
 i) a first promoter operably linked to a first gene, and
 ii) a second promoter operably linked to a second gene,
 wherein the second promoter is divergently coupled to the first promoter, and wherein the transcription of the operably linked second gene under the control of the second promoter is inhibited by negative supercoiling of the second promoter.

The polynucleotide can be an extra-chromosomal genetic material or integrated into the genome of the cell. Extra-chromosomal genetic material can be a circular plasmid, linear plasmid, cosmid, artificial chromosome vector, yeast cloning vector, mammalian vector, etc. Additional examples of extra-chromosomal genetic material are known to a skilled artisan and such embodiments are within the purview of the invention.

Incorporation into the genome of the cell can be at a specific location within the genome or a random location. Techniques for incorporating a polynucleotide into a specific location or a random location within the genome of a cell are well known in the art and such embodiments are within the purview of the invention.

In certain embodiments, at least the first promoter or the second promoter is operably linked to a heterologous gene. As such, certain embodiments of the invention provide a recombinant polynucleotide, which does not exist in nature.

In certain embodiments, the polynucleotides described herein further comprise one or more of: a terminator for one or both of the first and the second genes; a selectable marker, for example, an antibiotic resistance gene; an origin of replication for replication in a prokaryotic cell and/or a eukaryotic cell; a multiple cloning site. Additional DNA elements suitable for inclusion in the polynucleotides described herein are known to a skilled artisan and such embodiments are within the purview of the invention.

The first promoter can be a constitutive promoter or an inducible promoter. In certain embodiments, the first promoter is an inducible promoter under the control of an inducer. For example, the inducer can be IPTG and the promoter can be $P_{T7lac}$, $P_{trc}$, $P_{lac}$, $P_{T7A1/O4}$, or $P_{lacUV5}$. In further embodiments, the inducer is rhamnose, arabinose, tetracycline, or nalidixic acid and the corresponding promoter is $P_{rhaBAD}$, $P_{ara}$, $P_{tetA}$, or $P_{recA}$, respectively. In certain embodiments, the inducer is a condition, for example, phosphate starvation, tryptophan starvation, oxygen starvation, a temperature of about 40-45° C., a temperature of below 20° C., hyperosmolarity, glucose starvation and the corresponding promoter is $P_{phoA}$, $P_{trp}$, $P_{nar}$, $P_{PL}$, $P_{cspA}$, $P_{proU}$, or $P_{est-4}$, respectively. Additional examples of inducers and their corresponding inducible promoters are known to a person of ordinary skill in the art and such embodiments are within the purview of the invention.

The second promoter is divergently coupled to the first promoter and the transcription of the operably linked second gene under the control of the second promoter is inhibited by negative supercoiling of the second promoter. A non-limiting example of a promoter suitable for use as a second promoter includes $P_{gyrA}$ or $P_{gyrB}$.

The phrase "negative supercoiling of the second promoter" indicates that the region of DNA containing the second promoter is negatively supercoiled.

In certain embodiments, the first and/or the second gene each encode for a functional protein, particularly, a marker protein. Marker proteins useful in the methods described herein include an enzyme, an antibiotic resistance protein, or a florescent protein. Additional examples of marker proteins useful in the methods described herein are known to a person of ordinary skill in the art and such embodiments are within the purview of the invention.

In a particular embodiment, the first gene does not provide a marker protein and only the second gene provides a marker protein. In this case, the first gene may be a short segment of DNA, for example, between 10 to 200 nucleotides, which can be transcribed under the influence of the first promoter without providing a marker protein.

A gyrase inhibitor, in addition to enhancing the expression of second gene, may also inhibit the expression of the first gene. Therefore, in one embodiment, a compound is identified as:

i) a gyrase inhibitor, if the expression of the first gene is higher in the second portion compared to the expression of the first gene in the first portion, or i) not a gyrase inhibitor, if the expression of the first gene is not higher in the second portion compared to the expression of the first gene in the first portion.

Accordingly, in one embodiment, the second gene does not provide a marker protein and only the first gene provides a marker protein. In this case, the second gene may be a short segment of DNA, for example, between 10 to 200 nucleotides, which can be transcribed under the influence of the first promoter without providing a marker protein.

In one embodiment, a cell or a culture of the cell provided in step a) is further cultured in an appropriate medium under appropriate conditions to increase the number of cells in the culture. This step is optional; however, performing this step provides a fresh culture of cells that may be more responsive to a compound being tested and/or an inducer.

The first and the second portions as envisioned herein include two separate cultures that can be obtained in many ways. For example, a first portion can be a first culture provided in step a) and a second portion can be a second culture provided in step a). Alternately, a first portion can be a culture obtained by culturing a first cell or a first culture provided in step a) and a second portion can be a culture obtained by culturing a second cell or a second culture provided in step a). In a preferred embodiment, a first portion and a second portion are the portions of a culture obtained by culturing a cell or a culture provided in step a). In this embodiment, the first portion and the second portion contains cells that are identical in terms of metabolic activity, growth phase, gene expression, and other environmental factors that can affect the expressions of the first gene and the second gene. Additional embodiments of obtaining a first portion and a second portion suitable for use in the methods described herein can be readily envisioned by a skilled artisan and such embodiments are within the purview of the invention.

In a further embodiment, a first portion of the culture, provided in step a) or cultured in step b), is incubated in the presence of the compound, and a second portion of the culture, provided in step a) or cultured in step b), is incubated in the absence of the compound. In this step of incubation with or without the compound, an inducer can be added in both the first and the second portion if the first promoter is an inducible promoter. In embodiments where an inducer is a condition, the first and the second portions can be cultured under the inducing conditions. Optionally, when an inducer is used, a third portion of the culture, provided in step a) or cultured in step b), can be incubated in the absence of both the compound and the inducer. The third portion can provide control levels of expression for the first and/or the second genes.

The step of incubation can be performed at a suitable temperature that may be different from the temperature used for culturing the cell. For example, when the cell is $E.$ $coli$ and when an inducer is used, the step of incubation is carried out at a lower temperature of about 20° C.-30° C. compared to about 37° C. used for culturing. The step of incubation is performed for sufficient period of time which allows for the expression of the first and/or the second genes. The incubation step can be 30 minutes to 12 hours, one hour to ten hours, two hours to eight hours, three hours to seven hours, four hours to six hours, or about five hours. Appropriate incubation period depends on the first and the second promoters, first and the second genes, and the type of cell.

The step of measuring the expression of the first gene and/or the second gene in the first portion and/or the second portion after the incubation step c) depends on the product of the first and/or the second gene. For example, when the first and/or the second genes are enzymes, the enzymatic activity of the first and the second genes are measured. In embodiments where the first gene does not encode a marker protein, only the expression of the second gene is measured. In embodiments where the second gene does not encode a marker protein, only the expression of the first gene is measured.

Depending upon the level of expression of the first gene and/or the second gene in the first portion and the second portion, the compound being tested is identified as a gyrase inhibitor or not a gyrase inhibitor.

The transcription of the second gene under the control of the second promoter is inhibited by negative supercoiling of the second promoter. Negative supercoiling of the second promoter is caused by the induction of the expression of the first gene via the first promoter. A gyrase inhibitor inhibits the expression of the first gene thereby prevents negative supercoiling of the second promoter and in turn relieves the inhibition of the expression of the second gene. Therefore, if the expression of the second gene is higher in the first portion, i.e., in the presence of the compound, compared to the expression of the second gene in the second portion, i.e., in the absence of the compound, the compound is identified as a gyrase inhibitor. This relieving of inhibition of the second promoter and the resultant expression of the second gene can be referred to as a gyrase inhibitor mediated enhancement of the second gene expression.

Alternately, if the expression of the first gene is higher in the second portion, i.e., in the absence of the compound, compared to the expression of the first gene in the first portion, i.e., in the presence of the compound, the compound is a gyrase inhibitor.

A compound that is not a gyrase inhibitor cannot inhibit the expression of the first gene and cannot prevent negative supercoiling of the second promoter. Therefore, a compound that is not a gyrase inhibitor cannot relieve the inhibition of the expression of the second gene. Therefore, if the expression of the second gene is not higher in the first portion, i.e., in the presence of the compound, compared to the expression of the second gene in the second portion, i.e., in the absence of the compound, the compound is not a gyrase inhibitor.

Alternately, a compound that is not a gyrase inhibitor cannot inhibit the expression of the first gene. Therefore, if the expression of the first gene not higher in the second portion, i.e., in the absence of the compound, compared to the expression of the first gene in the first portion, i.e., in the presence of the compound, the compound is not a gyrase inhibitor.

In one embodiment, each compound from a library of compounds is identified as a gyrase inhibitor or not a gyrase inhibitor according to the methods described herein. When a library of compounds is used, typically, a high-throughput assay is used, for example, a multiwall format assay. For example, a multi-well plate can be used to screen a compound library where multiple wells of the multi-well plate correspond to a first portion of the culture, i.e., incubation in the presence of the compound and optionally, the inducer and one or more wells corresponds to a second portion of the culture, i.e., incubation in the absence of the compound and in the presence or absence of the inducer, as appropriate.

Accordingly, an embodiment of the invention provides a screening assay to identify one or more compounds from a plurality of compounds as gyrase inhibitors or not gyrase inhibitors, wherein the screening assay comprises the steps of:

a) providing a cell or a culture of the cell, wherein the cell comprises a polynucleotide comprising:
  i) a first promoter operably linked to a first gene, and
  ii) a second promoter operably linked to a second gene, wherein the second promoter is divergently coupled to the first promoter, and wherein the transcription of the operably linked second gene under the control of the second promoter is inhibited by negative supercoiling of the second promoter;
b) optionally, culturing the cell or the culture of the cell;
c) incubating a plurality of test portions of the culture, provided in step a) or cultured in step b), each test portion in the plurality of test portions in the presence of one compound from the plurality of compounds and incubating a control portion of the culture, provided in step a) or cultured in step b), in the absence of any compound from the plurality of compounds;
d) measuring the expression of the first gene and/or the second gene each of the plurality of test portions and/or the control portion after the incubation of step c); and
e) identifying each compound in the plurality of compounds as:
  i) a gyrase inhibitor, if the expression of the second gene is higher in the test portion compared to the expression of the second gene in the control portion, or
  i) not the gyrase inhibitor, if the expression of the second gene is not higher in the test portion compared to the expression of the second gene in the control portion.

As such, the assay of the invention can identify one or more compounds from a library of compounds as a gyrase inhibitor. A gyrase inhibitor identified according to the methods described herein can be used as an inhibitor of a cell, for example, a bacterial cell used in the assay.

Various aspects described above in connection with the method of identifying a compound as a gyrase inhibitor or not a gyrase inhibitor, for example, the type of cell, the first and the second promoters, the first and the second gene, etc., also apply to the screening assay described herein.

Further embodiments of the invention also provide an assay comprising the steps of:

a) providing a cell or a culture of the cell, wherein the cell comprises a polynucleotide comprising:
  i) a first promoter operably linked to a first gene, and
  ii) a second promoter operably linked to a second gene, wherein the second promoter is divergently coupled to the first promoter, and wherein the transcription of the operably linked second gene under the control of the second promoter is inhibited by negative supercoiling of the second promoter;
b) optionally, culturing the cell or the culture of the cell;
c) incubating a first portion of the culture, provided in step a) or cultured in step b), in the presence of the compound and incubating a second portion of the culture, provided in step a) or cultured in step b), in the absence of the compound;
d) measuring the expression of the first gene and/or the second gene in the first portion and/or the second portion after the incubation of step c).

Various aspects described above in connection with the method of identifying a compound as a gyrase inhibitor or not a gyrase inhibitor, for example, the type of cell, the first and the second promoters, the first and the second gene, etc., also apply to the assay described herein.

An even further embodiment of the invention provides a polynucleotide comprising:
  i) a first promoter operably linked to a first gene, and
  ii) a second promoter operably linked to a second gene, wherein the second promoter is divergently coupled to the first promoter, and wherein the transcription of the operably linked second gene under the control of the second promoter is inhibited by negative supercoiling of the second promoter.

The polynucleotide can be an extra-chromosomal genetic material or integrated into the genome of a cell. Extra-chromosomal genetic material can be a circular plasmid, linear plasmid, cosmid, artificial chromosome vector, yeast cloning vector, mammalian vector, etc. Additional examples of extra-chromosomal genetic material are known to a skilled artisan and such embodiments are within the purview of the invention.

Various aspects described above in connection with the method of identifying a compound as a gyrase inhibitor or not a gyrase inhibitor, for example, the first and the second promoters, the first and the second gene, inducers, etc., also apply to the polynucleotides described herein.

A further embodiment of the invention provides a cell comprising a polynucleotide comprising:
  i) a first promoter operably linked to a first gene, and
  ii) a second promoter operably linked to a second gene, wherein the second promoter is divergently coupled to the first promoter, and wherein the transcription of the operably linked second gene under the control of the second promoter is inhibited by negative supercoiling of the second promoter.

The types of cells and other aspects applicable to a cell as described above in connection with the method of identifying a compound as a gyrase inhibitor or not a gyrase inhibitor also apply to the cells described herein.

In one embodiments, the cell is a bacterial cell, particularly, *E. coli*. An embodiment provides *E. coli* strains described in Table 2.

Certain embodiments of the invention provide kits containing polynucleotides described herein, cells (with or without the polynucleotides described herein), and reagents for carrying out the assays of the invention. Various aspects described above in connection with the method of identifying a compound as a gyrase inhibitor or not a gyrase inhibitor, for example, the type of cell, the first and the second promoters, the first and the second gene, etc., also apply to the kits described herein.

Certain embodiments according to the instant disclosure are summarized below:

1. A method for identifying a compound as a gyrase inhibitor or not a gyrase inhibitor, the method comprising the steps of:
  a) providing a cell or a culture of the cell, wherein the cell comprises a polynucleotide comprising:
    i) a first promoter operably linked to a first gene, and
    ii) a second promoter operably linked to a second gene, wherein the second promoter is divergently coupled to the first promoter, and wherein the transcription of the operably linked second gene under the control of the second promoter is inhibited by negative supercoiling of the second promoter;

b) optionally, culturing the cell or the culture of the cell;

c) incubating a first portion of the culture, provided in step a) or cultured in step b), in the presence of the compound and incubating a second portion of the culture, provided in step a) or cultured in step b), in the absence of the compound;

d) measuring the expression of the first gene and/or the second gene in the first portion and/or the second portion after the incubation of step c); and e) identifying the compound as:
   i) the gyrase inhibitor:
      A) if the expression of the second gene is higher in the first portion compared to the expression of the second gene in the second portion, or
      B) if the expression of the first gene is higher in the second portion compared to the expression of the first gene in the first portion; or
   i) not the gyrase inhibitor:
      A) if the expression of the second gene is not higher in the first portion compared to the expression of the second gene in the second portion, or
      B) if the expression of the first gene is not higher in the second portion compared to the expression of the first gene in the first portion.

2. The method of embodiment 1, wherein the cell is a prokaryotic cell or a eukaryotic cell.

3. The method of embodiment 1, wherein the polynucleotide is an extra-chromosomal genetic material.

4. The method of embodiment 1, wherein the polynucleotide is integrated into the genome of the cell.

5. The method embodiment 1, wherein the polynucleotide further comprises one or more of: a terminator for one or both of the first and the second genes, a selectable marker, an origin of replication for replication in a prokaryotic cell and/or a eukaryotic cell, or a multiple cloning site.

6. The method of embodiment 1, wherein the first promoter is an inducible promoter under the control of an inducer.

7. The method of embodiment 6, wherein the first promoter is $P_{T7lac}$, $P_{trc}$, $P_{lac}$, $P_{T7A1/O4}$, $P_{lacUV5}$, $P_{rhaBAD}$, $P_{ara}$, $P_{tetA}$, $P_{recA}$, $P_{phoA}$, $P_{trp}$, $P_{nar}$, $P_{PL}$, $P_{cspA}$, $P_{proU}$, or $P_{est-4}$.

8. The method of embodiment 1, wherein the second promoter is $P_{gyrA}$ or $P_{gyrB}$.

9. The method of embodiment 1, wherein the first and/or the second gene each encodes for a marker protein.

10. The method of embodiment 1, wherein only the first gene or only the second gene encodes for a marker protein.

11. A cell or a culture of the cell, wherein the cell comprises a polynucleotide comprising:
   i) a first promoter operably linked to a first gene, and
   ii) a second promoter operably linked to a second gene,
   wherein the second promoter is divergently coupled to the first promoter, and wherein the transcription of the operably linked second gene under the control of the second promoter is inhibited by negative supercoiling of the second promoter;

12. The cell of embodiment 11, wherein the cell is a prokaryotic cell or a eukaryotic cell.

13. The cell of embodiment 11, wherein the polynucleotide is an extra-chromosomal genetic material.

14. The cell of embodiment 11, wherein the polynucleotide is integrated into the genome of the cell.

15. The cell of embodiment 11, wherein the polynucleotide further comprises one or more of: a terminator for one or both of the first and the second genes, a selectable marker, an origin of replication for replication in a prokaryotic cell and/or a eukaryotic cell, or a multiple cloning site.

16. The cell of embodiment 11, wherein the first promoter is an inducible promoter under the control of an inducer.

17. The cell of embodiment 16, wherein the first promoter is $P_{T7lac}$, $P_{trc}$, $P_{lac}$, $P_{T7A1/O4}$, $P_{lacUV5}$, $P_{rhaBAD}$, $P_{ara}$, $P_{tetA}$, $P_{recA}$, $P_{phoA}$, $P_{trp}$, $P_{nar}$, $P_{PL}$, $P_{cspA}$, $P_{proU}$, or $P_{est-4}$.

18. The cell of embodiment 11, wherein the second promoter is $P_{gyrA}$ or $P_{gyrB}$.

19. The cell of embodiment 11, wherein the first and/or the second gene each encodes for a marker protein.

20. The cell of embodiment 11, wherein only the first gene or only the second gene encodes for a marker protein.

21. A polynucleotide comprising:
   i) a first promoter operably linked to a first gene, and
   ii) a second promoter operably linked to a second gene,
   wherein the second promoter is divergently coupled to the first promoter, and wherein the transcription of the operably linked second gene under the control of the second promoter is inhibited by negative supercoiling of the second promoter;

22. The polynucleotide of embodiment 21, wherein the polynucleotide further comprises one or more of: a terminator for one or both of the first and the second genes, a selectable marker, an origin of replication for replication in a prokaryotic cell and/or a eukaryotic cell, or a multiple cloning site.

23. The polynucleotide of embodiment 21, wherein the first promoter is an inducible promoter under the control of an inducer.

24. The polynucleotide of embodiment 23, wherein the first promoter is $P_{T7lac}$, $P_{trc}$, $P_{lac}$, $P_{T7A1/O4}$, $P_{lacUV5}$, $P_{rhaBAD}$, $P_{ara}$, $P_{tetA}$, $P_{recA}$, $P_{phoA}$, $P_{trp}$, $P_{nar}$, $P_{PL}$, $P_{cspA}$, $P_{proU}$, or $P_{est-4}$.

25. The polynucleotide of embodiment 21, wherein the second promoter is $P_{gyrA}$ or $P_{gyrB}$.

26. The polynucleotide of embodiment 21, wherein the first and/or the second gene each encodes for a marker protein.

27. The polynucleotide of embodiment 21, wherein only the first gene or only the second gene does not encode for a marker protein.

28. A screening assay to identify one or more compounds from a plurality of compounds, wherein the screening assay comprises the steps of:

a) providing a cell or a culture of the cell, wherein the cell comprises a polynucleotide comprising:
   i) a first promoter operably linked to a first gene, and
   ii) a second promoter operably linked to a second gene,
   wherein the second promoter is divergently coupled to the first promoter, and wherein the transcription of the operably linked second gene under the control of the second promoter is inhibited by negative supercoiling of the second promoter;

b) optionally, culturing the cell or the culture of the cell;

c) incubating a plurality of test portions of the culture, provided in step a) or cultured in step b), each test portion in the plurality of test portions in the presence of one compound from the plurality of compounds and incubating a control portion of the culture, provided in step a) or cultured in step b), in the absence of any compound from the plurality of compounds;

d) measuring the expression of the first gene and/or the second gene each of the plurality of test portions and/or the control portion after the incubation of step c); and e) identifying each compound in the plurality of compounds as:
   i) the gyrase inhibitor:
      A) if the expression of the second gene is higher in the test portion compared to the expression of the second gene in the control portion, or
      B) if the expression of the first gene is higher in the control portion compared to the expression of the first gene in the test portion; or
   i) not the gyrase inhibitor:
      A) if the expression of the second gene is not higher in the test portion compared to the expression of the second gene in the control portion, or B) if the expression of the first gene is not higher in the control portion compared to the expression of the first gene in the test portion.

29. The method of embodiment 28, wherein the cell is a prokaryotic cell or a eukaryotic cell.

30. The method of embodiment 28, wherein the polynucleotide is an extra-chromosomal genetic material.

31. The method of embodiment 28, wherein the polynucleotide is integrated into the genome of the cell.

32. The method embodiment 28, wherein the polynucleotide further comprises one or more of: a terminator for one or both of the first and the second genes, a selectable marker, an origin of replication for replication in a prokaryotic cell and/or a eukaryotic cell, or a multiple cloning site.

33. The method of embodiment 28, wherein the first promoter is an inducible promoter under the control of an inducer.

34. The method of embodiment 33, wherein the first promoter is $P_{T7lac}$, $P_{trc}$, $P_{lac}$, $P_{T7A1/O4}$, $P_{lacUV5}$, $P_{rhaBAD}$, $P_{ara}$, $P_{tetA}$, $P_{recA}$, $P_{phoA}$, $P_{trp}$, $P_{nar}$, $P_{PL}$, $P_{cspA}$, $P_{proU}$, or $P_{cst-4}$.

35. The method of embodiment 28, wherein the second promoter is $P_{gyrA}$ or $P_{gyrB}$.

36. The method of embodiment 28, wherein the first and/or the second gene each encodes for a marker protein.

37. The method of embodiment 28, wherein the first gene does not encode for a functional or detectable protein.

38. A method comprising the steps of:
    a) providing a cell or a culture of the cell, wherein the cell comprises a polynucleotide comprising:
       i) a first promoter operably linked to a first gene, and
       ii) a second promoter operably linked to a second gene,
       wherein the second promoter is divergently coupled to the first promoter, and wherein the transcription of the operably linked second gene under the control of the second promoter is inhibited by negative supercoiling of the second promoter;
    b) optionally, culturing the cell or the culture of the cell;
    c) incubating a first portion of the culture, provided in step a) or cultured in step b), in the presence of the compound and incubating a second portion of the culture, provided in step a) or cultured in step b), in the absence of the compound;
    d) measuring the expression of the first gene and/or the second gene in the first portion and/or the second portion after the incubation of step c).

39. The method of embodiment 38, wherein the cell is a prokaryotic cell or a eukaryotic cell.

40. The method of embodiment 38, wherein the polynucleotide is an extra-chromosomal genetic material.

41. The method of embodiment 38, wherein the polynucleotide is integrated into the genome of the cell.

42. The method embodiment 38, wherein the polynucleotide further comprises one or more of: a terminator for one or both of the first and the second genes, a selectable marker, an origin of replication for replication in a prokaryotic cell and/or a eukaryotic cell, or a multiple cloning site.

43. The method of embodiment 38, wherein the first promoter is an inducible promoter under the control of an inducer.

44. The method of embodiment 43, wherein the first promoter is $P_{T7lac}$, $P_{trc}$, $P_{lac}$, $P_{T7A1/O4}$, $P_{lacUV5}$, $P_{rhaBAD}$, $P_{ara}$, $P_{tetA}$, $P_{recA}$, $P_{phoA}$, $P_{trp}$, $P_{nar}$, $P_{PL}$, $P_{cspA}$, $P_{proU}$, or $P_{cst-4}$.

45. The method of embodiment 38, wherein the second promoter is $P_{gyrA}$ or $P_{gyrB}$.

46. The method of embodiment 38, wherein the first and/or the second gene each encodes for a marker protein.

47. The method of embodiment 38, wherein only the first gene or only the second gene does not encode for a marker protein.

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising." The transitional terms/phrases (and any grammatical variations thereof) "comprising", "comprises", "comprise", "consisting essentially of", "consists essentially of", "consisting" and "consists" can be used interchangeably.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of compositions containing amounts of ingredients where the term "about" is used, these compositions contain the stated amount of the ingredient with a variation (error range) of 0-10% around the value (X+10%).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

When ranges are used herein, such as for dose ranges, combinations and subcombinations of ranges (e.g., subranges within the disclosed range), specific embodiments therein are intended to be explicitly included.

Materials and Methods

Proteins, Chemicals, and Reagents

Ethidium bromide, Kanamycin, and lysozyme were purchased from Sigma-Aldrich Corporation (St. Louis, Mo.). Ampicillin and bovine serum albumin (BSA) were obtained from Fisher Scientific (Fairlawn, N.J.). Isopropyl-β-D-thiogalactopyranoside (IPTG) was obtained from Anatrace, Inc (Maumee, Ohio). All restriction enzymes, T4 DNA ligase, T4 polynucleotide kinase, and E. coli DNA gyrase were bought from New England Biolabs (Beverly, Mass.). Pfu DNA polymerase was purchased from Stratagene, Inc. (La Jolla, Calif.). All synthetic oligonucleotides were obtained from MWG-Biotech, Inc. (Huntsville, Ala.). QIAprep Spin Miniprep Kit, QIAquick Gel Extraction Kit, RNeasy Mini Kit, and QIAquick Nucleotide Removal Kit were bought from QIAGEN, Inc. (Valencia, Calif.). ThermoScript RT-PCR System plus Platinum® Taq DNA polymerase was purchased from Invitrogen, Inc. (Carlsbad, Calif.). Power SYBR Green PCR Master Mix was obtained from Applied Biosystems, Inc. (Carlsbad, Calif.). Luciferase Assay System is a product of Promega Corporation (Madison, Wis.). SYBR® Gold Nucleic Acid Gel Stain was purchased from Life Technologies (Grand Island, N.Y.).

Plasmid DNA Templates

All circular plasmids are derived from plasmid pBR322. Construction of plasmid DNA templates sometimes required DNA fusions between noncomplementary cohesive termini. In this scenario, cohesive ends were converted before ligation to blunt ends by incubation of the DNA fragments with T4 DNA polymerase in the presence of dNTPs. Plasmids pZXD99, pZXD133, pZXD145, and pZXD146 were described previously. Plasmid pZXD144 was constructed by inserting a 70 bp synthetic DNA fragment carrying $P_{gyrA}$ between BamHI and HindIII sites. Plasmid pZXD147 was made in two steps. First, an 87 bp synthetic DNA oligomer containing $P_{lac}$ was inserted between the EcoRI and XhoI sites of pZXD99 to generate pZXD108. Then a 3,093 bp PCR product containing the lacZ gene amplified from MG1655 genomic DNA was cloned into the AgeI and BsmI sites of pZXD105 to yield pZXD147.

All linear plasmids were derived from coliphage N15-based, linear plasmid pZXD4 described previously (30). Plasmid pZXD103 was made by the insertion of a 6,763 bp BglII-SpeI DNA fragment of pZXD99 into the BglII and NheI sites of pZXD4. Plasmid pZXD143 was constructed by inserting a 6,807 bp BglII-SpeI fragment into the BglII and NheI sites of pZXD4. Plasmid pZXD150 was created by inserting a 6,817 bp BglII-SpeI DNA fragment of pZXD144 into the BglII and NheI sites of pZXD4. Plasmid pZXD151 was constructed by inserting a 6,837 bp BglII-SpeI fragment of pZXD145 into the BglII and NheI sites of pZXD4. Plasmid pZXD152 was made by the inserting of a 6,839 bp BglII-SpeI fragment of pZXD146 into the BglII and NheI sites of pZXD4.

Plasmid pZXD153 was created by the insertion of a 6,839 bp BglII-SpeI fragment of pZXD147 into the BglII and NheI sites of pZXD4. Properties of plasmids are summarized in Table 1.

TABLE 1

Plasmids used in this study

| Plasmid | Type | [a]Promoter 1 | [b]Promoter 2 | Source |
|---|---|---|---|---|
| pZXD99 | Circular | $P_{T7}$ | $P_{leu-500}$ | 30 |
| pZXD133 | Circular | $P_{T7A1/O4}$ | $P_{leu-500}$ | 30 |
| pZXD144 | Circular | $P_{T7A1/O4}$ | $P_{gyrA}$ | This disclosure |
| pZXD145 | Circular | $P_{tac}$ | $P_{leu-500}$ | 30 |
| pZXD146 | Circular | $P_{lacUV5}$ | $P_{leu-500}$ | 30 |
| pZXD147 | Circular | $P_{lac}$ | $P_{leu-500}$ | This disclosure |
| pZXD103 | Linear | $P_{T7}$ | $P_{leu-500}$ | This disclosure |
| pZXD143 | Linear | $P_{T7A1/O4}$ | $P_{leu-500}$ | This disclosure |
| pZXD150 | Linear | $P_{T7A1/O4}$ | $P_{gyrA}$ | This disclosure |
| pZXD151 | Linear | $P_{tac}$ | $P_{leu-500}$ | This disclosure |
| pZXD152 | Linear | $P_{lacUV5}$ | $P_{leu-500}$ | This disclosure |
| pZXD153 | Linear | $P_{lac}$ | $P_{leu-500}$ | This disclosure |

[a]Promoter controls the expression of β-galactosidase.
[b]Promoter 2 controls the expression of firefly luciferase.

Bacterial Strains

*Escherichia coli* strains MG1655 [F⁻, λ⁻, rph-I] and VS111[F⁻, λ⁻, rph-I, ΔtopA] were obtained from the Coli Genetic Stock Collection/*E. coli* Genetic Resource Center (CGSC) at Yale University. MG1655 (DE3), VS111 (DE3), FL1130, and FL1131 were described previously (Fulcrand et al., Zhi et al., and Samul et al.). *E. coli* strains FL1181 (MG1655 (DE3) ΔlacZ attnT7::$P_{T7A1/O4}$-lacZ $P_{gyrA}$-luc) and FL1182 (VS111(DE3) 4lacZ attnT7::$P_{T7A1/O4}$-lacZ $P_{gyrA}$-luc) were constructed by using a Tn7-based site-specific recombination system.

Briefly, a 5.1 kb DNA fragment carrying the divergently coupled $P_{gyrA}$ and $P_{T7A1/O4}$ promoters with the luc and lacZ genes was inserted to the attTn7 site of the *E. coli* chromosome (84 min of the chromosome) to generate FL1181 and FL1182. In both strains, the IPTG-inducible $P_{T7A1/O4}$ controls the expression of β-galactosidase. Using similar approach, the following *E. coli* strains were generated: FL1181, FL1182, FL1198, FL1199, FL1200, FL1202, FL1203, and FL1204. The genotype of these strains and other properties are summarized in Table 2.

TABLE 2

*E. coli* strains described in this disclosure

| Strain | Genotype | [a]Promoter 1 | [b]Promoter 2 | Source |
|---|---|---|---|---|
| FL1130 | MG1655(DE3)ΔlacZ attTn7::$P_{T7A1/O4}$lacZ-$P_{leu-500}$luc | $P_{T7A1/O4}$ | $P_{leu-500}$ | 30 |
| FL1131 | VS111(DE3)ΔlacZ attTn7::$P_{T7A1/O4}$lacZ-$P_{leu-500}$luc | $P_{T7A1/O4}$ | $P_{leu-500}$ | 30 |
| FL1181 | MG1655(DE3)ΔlacZ attTn7::$P_{T7A1/O4}$lacZ-$P_{gyrA}$luc | $P_{T7A1/O4}$ | $P_{gyrA}$ | This study |
| FL1182 | VS111(DE3)ΔlacZ attTn7::$P_{T7A1/O4}$lacZ-$P_{gyrA}$luc | $P_{T7A1/O4}$ | $P_{gyrA}$ | This study |
| FL1198 | MG1655(DE3)ΔlacZ attTn7::$P_{tac}$-$P_{leu-500}$luc | $P_{tac}$ | $P_{leu-500}$ | This study |
| FL1199 | MG1655(DE3)ΔlacZ attTn7::$P_{lacUC5}$-$P_{leu-500}$luc | $P_{lacUV5}$ | $P_{leu-500}$ | This study |
| FL1200 | MG1655(DE3)ΔlacZ attTn7::$P_{lac}$-$P_{leu-500}$luc | $P_{lac}$ | $P_{leu-500}$ | This study |
| FL1202 | VS111(DE3)ΔlacZ attTn7::$P_{tac}$-$P_{leu-500}$luc | $P_{tac}$ | $P_{leu-500}$ | This study |
| FL1203 | VS111(DE3)ΔlacZ attTn7::$P_{lacUV5}$-$P_{leu-500}$luc | $P_{lacUV5}$ | $P_{leu-500}$ | This study |
| FL1204 | VS111(DE3)ΔlacZ attTn7::$P_{lac}$-$P_{leu-500}$luc | $P_{lac}$ | $P_{leu-500}$ | This study |

TABLE 2-continued

E. coli strains described in this disclosure

| Strain | Genotype | [a]Promoter 1 | [b]Promoter 2 | Source |
|---|---|---|---|---|
| FL1261 | MG1655(DE3)ΔlacZ attTn7::rrnBP$_1$,P$_{2/lacO1}$lacZ-P$_{leu-500}$luc | rrnBP$_1$,P$_2$/lacO1 | P$_{leu-500}$ | This study |
| FL1262 | VS111(DE3)ΔlacZ attTn7::rrnBP$_1$,P$_{2/lacO1}$lacZ-P$_{leu-500}$luc | rrnBP$_1$,P$_2$/lacO1 | P$_{leu-500}$ | This study |

[a]Promoter controls the expression of β-galactosidase.
[b]Promoter 2 controls the expression of firefly luciferase.

The Expression of β-Galactosidase

The expression level of β-galactosidase was measured by Miller's assay as described by Miller et al. Briefly, 100 mL of LB was inoculated with 1 mL of overnight bacterial cell culture until OD600 reaches about 0.2. 100 µL of bacterial cell culture was mixed with 900 µL of Z-buffer (60 mM Na$_2$HPO$_4$, 40 mM NaH$_2$PO$_4$, 10 mM KCl, 1 mM MgSO$_4$, and 50 mM β-mercaptoethanol). Cells were lysed with 60 µL of chloroform and 30 µL of 0.1% SDS. After cell lysates were equilibrated at 30° C. for five minutes, 200 µL of 4 mg/mL ONPG was added to the cell lysates. After additional 15 min incubation at 30° C., reactions were stopped by addition of 500 µL of 1 M Na$_2$CO$_3$. After cell debris was removed by centrifugation at 13,000 rpm for 1 min, OD420 and OD550 were measured in a Cary 50 spectrophotometer. β-Galactosidase activities (E) were calculated using the following equation:

$$E = 1000 \times \frac{OD_{420} - 1.75 \times OD_{550}}{t \times v \times OD_{600}} \quad (1)$$

where t and v represent reaction time and cell culture volume, respectively.

Luciferase Assay

Luciferase Assay was used to verify the expression of luciferase in various E. coli strains carrying different plasmid DNA templates. Briefly, E. coli cells carrying different plasmids were grown overnight in LB. Antibiotics were added to LB as needed. The overnight culture was then diluted (1:100) in fresh LB in the presence of different concentrations of IPTG, and grown until the OD600 nm reached approximately 0.5. Next, 50 µl of cells were mixed with 10 µl of 1 M K$_2$HPO$_4$ (pH 7.8) and 20 mM EDTA, quickly frozen in liquid nitrogen for 3 min, and equilibrated to room temperature for 30 min to yield about 60 µl of cell lysate. Then, the cell lysate was added with 300 µl freshly prepared lysis mix containing 1× cell culture lysis reagent (CCLR), 1.25 mg/ml lysozyme, and 2.5 mg/ml BSA, and incubated for 10 min at room temperature. Finally, 100 µl of Luciferase Assay Reagent (Promega Corporation, Madison, Wis.) was added to 20 µl of the cell lysate and used for light measurement by using a Promega GloMax 20/20 Single-Tube Luminometer.

RNA Isolation, cDNA Synthesis, and Polymerase Chain Reaction (PCR)

Total RNA was isolated from E. coli cells using QIAGEN RNeasy Kit as described by the manufacturer. To determine the integrity of the total RNA samples, 16S and 23S rRNA were resolved by electrophoresis in a 1.2% agarose gel in 1×MOPS buffer containing formaldehyde (20 mM MOPS, 8 mM sodium acetate anhydrous and 1 mM EDTA, pH 7.0, and 1% formaldehyde). After electrophoresis, agarose gels were stained with ethidium bromide, destained, and photographed under UV light. cDNAs were synthesized from total RNA samples using ThermoScript RT-PCR System. 2.76 µg of RNA was mixed with random hexamer primers (50 ng/µl) and four deoxynucleotide triphosphates (dNTPs; final concentration: 1 mM). The mixtures were incubated at 65° C. for 5 min and transferred on ice for another 5 min to remove secondary structures of RNA. The denatured RNA samples were then mixed with 1×cDNA synthesis buffer with a total volume of 20 µl containing 5 mM DTT, 40 units of RNaseOut, and 15 units of ThermoScript Reverse Transcriptase, and incubated at 25° C. for 10 min followed by 50° C. for 50 min to synthesize cDNAs. The cDNA synthesis mixtures were transferred to an 85° C. water bath for 5 min to terminate the reactions. After the synthesis step, 2 units of RNase H were added into the reaction mixtures and incubated at 37° C. for 20 min to remove the RNA templates.

PCR Reactions were carried out using cDNA samples synthesized as described above. A 50 µl PCR reaction contains 1×PCR Buffer without Mg$^{2+}$, 1 mM MgCl$_2$, 0.2 mM dNTPs, 0.2 µM of each primer, 0.5 µl cDNA and 2 units of Platinum Taq DNA polymerase. The reactions started at 94° C. for 2 min, proceeded 16 cycles (for linear plasmids, used 21 cycles instead) of 94° C. for 30 sec, 55° C. for 30 sec and 72° C. for 1 min, and terminated at 72° C. for 10 min. Subsequently, the PCR products were analyzed by electrophoresis in a 12% polyacrylamide gel in 1×TAE buffer. After electrophoresis, polyacrylamide gels were stained with ethidium bromide, destained, and photographed under UV light.

Real-Time PCR Assays

Real-time PCR assays were carried out using MiniOpticon Real-time PCR system (Bio-rad, Hercules, Calif.). A 20 µl reaction contains 1 µl cDNA, 0.5 µM of each primer and 10 µl of Power SYBR Green PCR Master Mix (2×). The reaction started at 95° C. for 10 min and continued for 40 cycles at 95° C. for 15 s and 60° C. for 1 min. The C$_q$ values (quantification cycle values) were calculated from exponential phase of each PCR amplification reaction as recommended by the manufacturer. Primers used in the RT-PCR reactions were summarized in Table 3.

TABLE 3

DNA oligonucleotides used for primers of the RT-PCR experiments

| Oligo[a] | Sequence (5'-3') | Location in the gene | Gene | PCR products (bp) | SEQ ID NO: |
|---|---|---|---|---|---|
| FL692F | AACAACGGCGGCGGGA AGTTCA | 1433-1455 | luc | 178 | 7 |
| FL693R | GGGACGAAGACGAACA CTTCTT | 1277-1299 | luc | 178 | 8 |

TABLE 3 -continued

DNA oligonucleotides used for primers of the RT-PCR experiments

| Oligo[a] | Sequence (5'-3') | Location in the gene | Gene | PCR pro-ducts (bp) | SEQ ID NO: |
|---|---|---|---|---|---|
| FL586F | AGTTATCCCCCTCCATCAGG | 154-135 | 16S | 99 | 9 |
| FL587R | TGCAAGTCGAACGGTAACAG | 56-75 | 16S | 99 | 10 |
| FL594F | ATTATGGCCCACACCAGTGGCG | 2917-2939 | LacZ | 173 | 11 |
| FL595R | TGACGGGCTCCAGGAGTCGTC | 3069-3089 | LacZ | 173 | 12 |

[a]FLXXXF and FLXXXR represent the forward and reverse primers of the PCR reactions, respectively.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Potent Activation of $P_{leu\text{-}500}$ by Divergently Coupled Transcription Initiated from a Strong Promoter Such as $P_{T7A1/O4}$ and the rrnB P1 and P2 Promoters An in vivo system to study the activation of supercoiling-sensitive $P_{leu\text{-}500}$ by divergently coupled transcription is described. The system comprises E. coli topA strain VS111 (DE3) ΔlacZ or wild-type strain MG1655(DE3) ΔlacZ and a circular plasmid or a linear plasmid. For plasmid DNA templates, $P_{leu\text{-}500}$ was divergently coupled to the strong IPTG-inducible $P_{T7A1/O4}$ (FIG. 1). The distance between these two promoters is 81 bp (the distance was calculated between the −35 regions of two promoters; FIG. 1B).

Figure 1C:
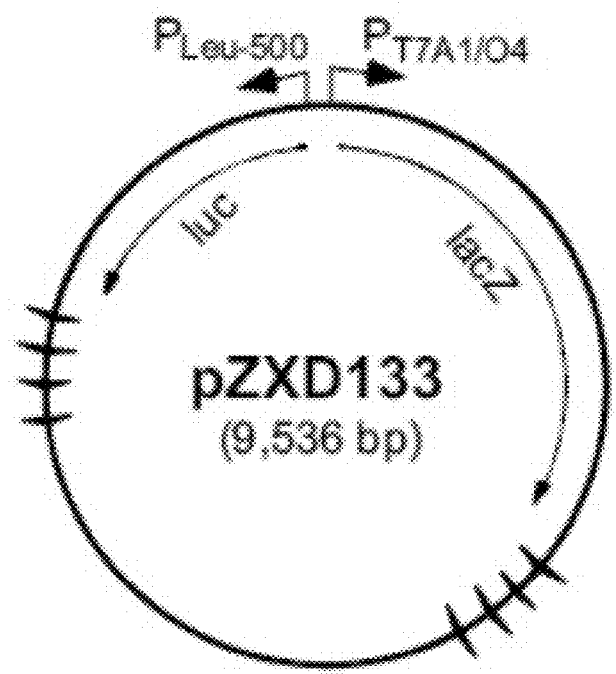
Figure 1D:
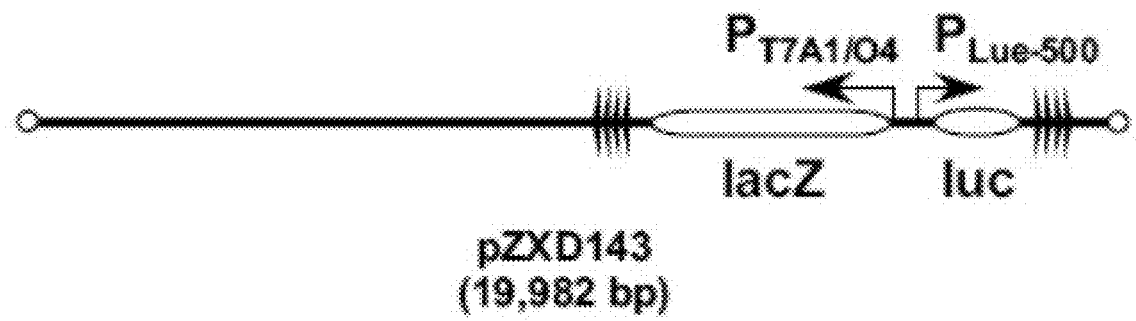

Additionally, two sets of four Rho-independent, rrnB T1 transcription terminators were used to stop transcription from the $P_{T7A1/O4}$ and $P_{leu\text{-}500}$, respectively (FIGS. 1C and D). In this way, transcription was restricted to selected regions of the plasmids. A luc gene (to express firefly luciferase) was cloned under the control of $P_{leu\text{-}500}$ and a lacZ gene under the control of $P_{T7A1/O4}$. Since lacZ deletion mutants were used, transcription levels of lacZ from $P_{T7A1/O4}$ were determined by measuring β-galactosidase activity. These two plasmids were transformed into VS111 (DE3) ΔlacZ or MG1655(DE3) ΔlacZ. After addition of IPTG to the cell culture in early log phase, the activation of $P_{leu\text{-}500}$ was monitored by measuring luciferase activities and also by determining transcription levels using RT-PCR assays. Results in FIG. 2 demonstrated that the divergently coupled transcription provided by E. coli RNA polymerase potently activated the supercoiling-sensitive $P_{leu\text{-}500}$. For instance, transcription by E. coli RNA polymerase on the circular plasmid pZXD133 activated $P_{leu\text{-}500}$ approximately 7.3 and 2.5 fold in VS111(DE3) ΔlacZ and MG1655 (DE3) ΔlacZ, respectively (FIG. 2B).

Transcription on the linear plasmid pZXD103 also activated $P_{leu\text{-}500}$ approximately 9.7 and 3.5 fold in VS111 (DE3) ΔlacZ and MG1655 (DE3) ΔlacZ, respectively (FIG. 2D). Since the basal expression of lacZ (β-galactosidase) in the absence of IPTG is always higher for the wild-type strain (MG1655) than for a topA mutant strain (VS111), these results demonstrate that the activation level of $P_{leu\text{-}500}$ correlates with the transcription level from $P_{T7A1/O4}$, disregarding the genetic backgrounds of host strains (FIGS. 2 and 7). In other words, a higher expression of β-galactosidase always corresponded to a higher expression of firefly luciferase (FIGS. 2 and 7).

To extend these findings to the chromosome level, a procedure for site-specific insertion of transgenes into the E. coli chromosome using transposon Tn7 was developed. Using this method, the divergently coupled $P_{leu\text{-}500}$ and $P_{T7A1/O4}$ promoters with the luc and lacZ genes (FIG. 1A) were inserted to the attTn7 site of the E. coli chromosome (84 min of the chromosome; Waddell et al.). Transcription provided by E. coli RNA polymerase greatly activated $P_{leu\text{-}500}$ on the chromosome. For instance, transcription via $P_{leu\text{-}500}$ was activated about 18 and 6 fold in VS111 and MG1655, respectively (FIG. 2F). In contrast, IPTG did not activate the $P_{leu\text{-}500}$ in the absence of a divergently coupled $P_{T7A1/O4}$. Again, the activation level of $P_{leu\text{-}500}$ correlated with the transcription level from $P_{T7A1/O4}$, disregarding the genetic backgrounds of the host strains (FIGS. 2E and F). Similar results were obtained if E. coli ribosomal rrnB P1 and P2 promoters were used to replace $P_{T7A1/O4}$ (FIG. 7).

Example 2—Transcription Activation of $P_{leu\text{-}500}$ is Dependent on the Promoter Strength To test how promoters with different strengths activated the divergently coupled $P_{leu\text{-}500}$, four IPTG-inducible promoters with different strengths, namely, $P_{T7A1/O4}$, $P_{tac}$, $P_{lacUV5}$, and $P_{lac}$ were used. These promoters were placed divergently to $P_{leu\text{-}500}$ and used to control the transcription and expression of lacZ (FIG. 8). Their effects on transcription at three different levels were tested: circular plasmid, linear plasmid, and chromosome. All promoters substantially activated the divergently coupled $P_{leu\text{-}500}$ in both topA and wild-type strains (FIGS. 3 and 9). The activation level was proportional to the promoter strength: stronger promoter provided higher activation (FIGS. 3 and 9). Transcription via divergently coupled promoters was also activated in E. coli. The activation of $P_{leu\text{-}500}$ was more potent at the chromosomal level than that at the plasmid levels for both strains tested (FIGS. 3 and 9). Nevertheless, differences were observed between the two E. coli strains tested. For instance, in the topA strain, the activation level almost linearly correlated with the promoter strength (FIG. 3D). In contrast, the strong artificial $P_{tac}$ only slightly activated the divergently coupled $P_{leu\text{-}500}$ in the wild-type strain (FIG. 9). A higher expression of β-galactosidase always corresponded to a higher expression of firefly luciferase, independent of the host genetic background although the fold of activation could be substantially different (FIGS. 3 and 9).

Example 3—Transcription by T7 RNA Polymerase Also Strongly Activated the Divergently Coupled $P_{leu\text{-}500}$ To examine whether transcription by a different RNA polymerase, for example, T7 RNA polymerase, also activated the divergently coupled $P_{leu\text{-}500}$ in E. coli, a circular (pZXD99) and a linear (pZXD103) plasmid DNA template (FIG. 10) that carry a T7 promoter divergently coupled to $P_{leu-500}$ were constructed. These two plasmids were transformed into VS111(DE3) or MG1655(DE3). After the addition of IPTG to the cell culture in early log phase, the activation of $P_{leu-500}$ was monitored by measuring the luciferase activity and also by determining transcription level using RT-PCR assays. FIG. 4 demonstrated that the divergently coupled transcription provided by T7 RNA polymerase activated the supercoiling-sensitive $P_{leu-500}$. For example, transcription by T7 RNA polymerase on the circular plasmid pZXD99 activated the transcription via $P_{leu-500}$ approximately 8.0 and 2.2 fold in VS111(DE3) and MG1655(DE3), respectively (FIG. 4A). Transcription by T7 RNA polymerase on the linear plasmid pZXD103 activated $P_{leu-500}$ mediated transcription by about 4.0 and 1.6 fold in VS111 (DE3) and MG1655 (DE3), respectively (FIG. 4B). These results suggest that the activation of $P_{leu-500}$ by divergently coupled transcription was independent of RNA polymerase employed in the experiment.

Figure 5A:
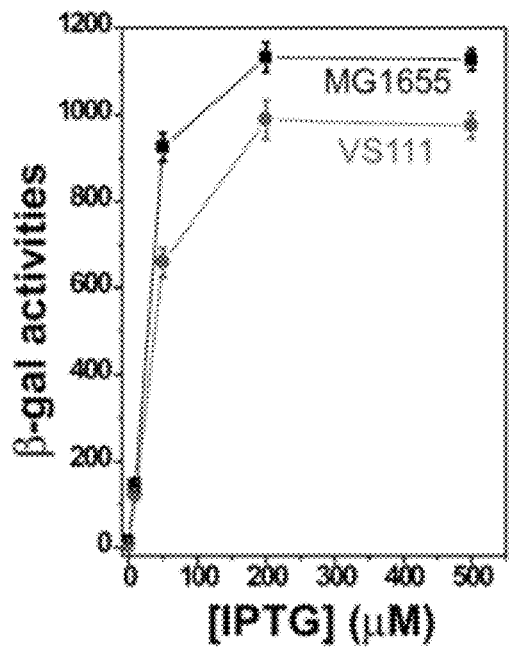
Figure 5B:
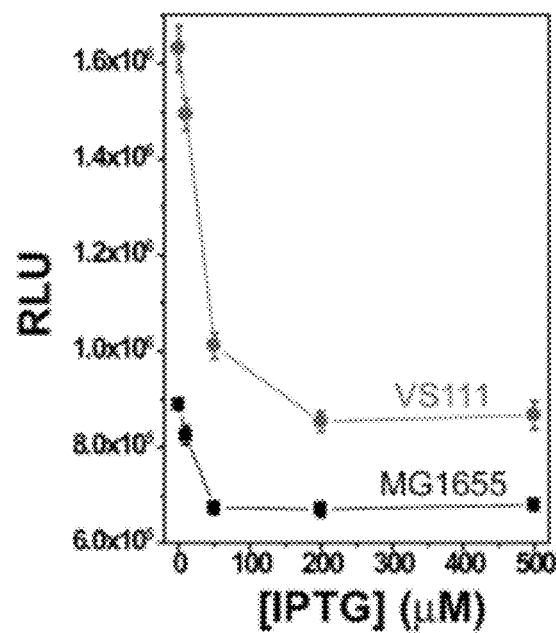
Figure 5C:
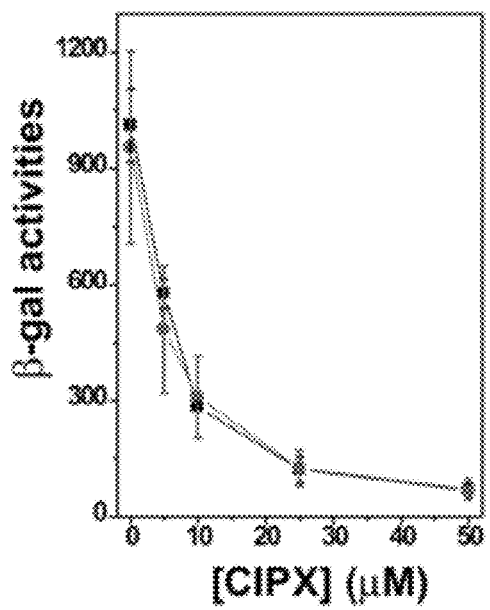
Figure 5D:
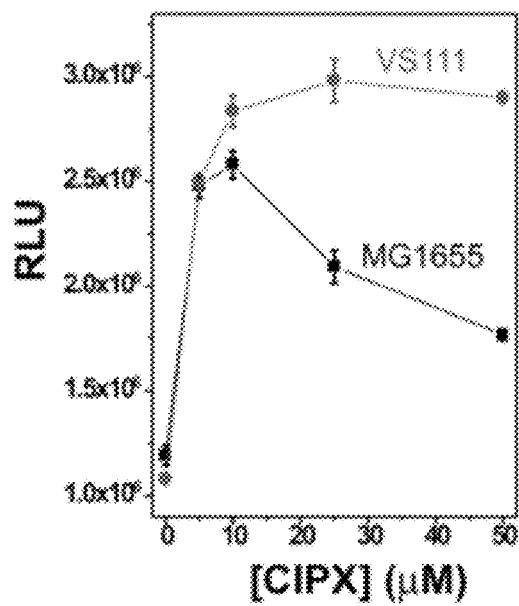
Figures 11A, 11B:
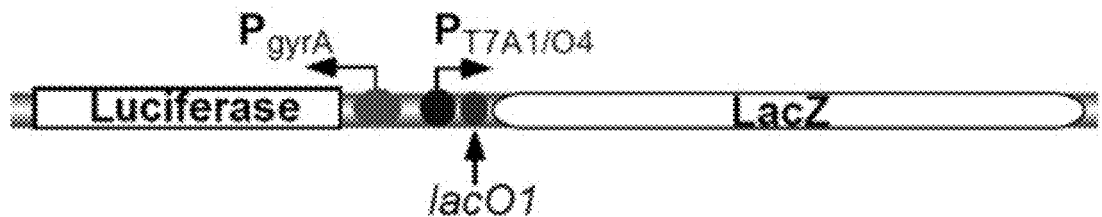
Figure 11C:
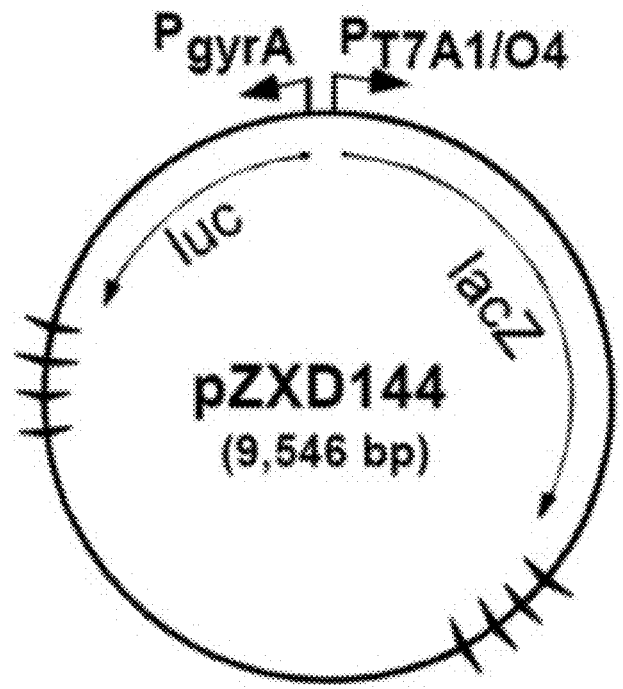
Figure 11D:
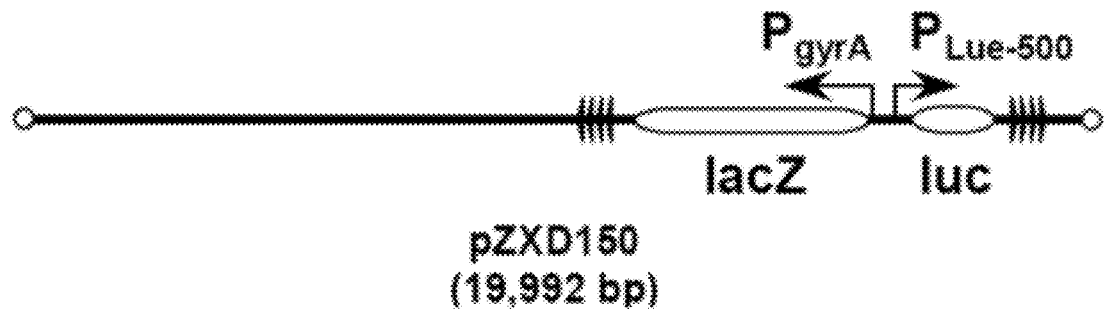
Figure 13B:
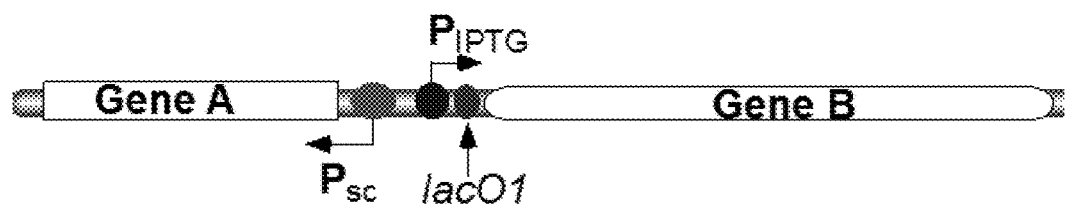
Figure 13C:
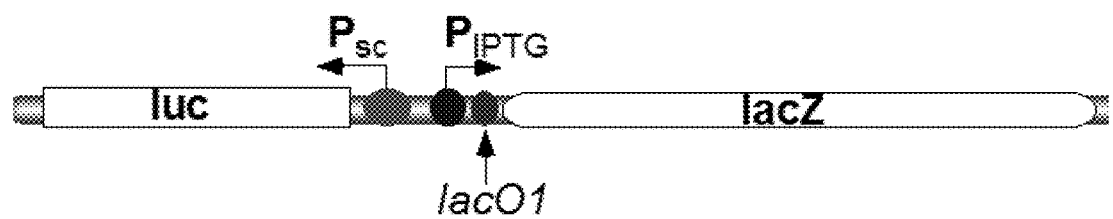
Figure 13D:
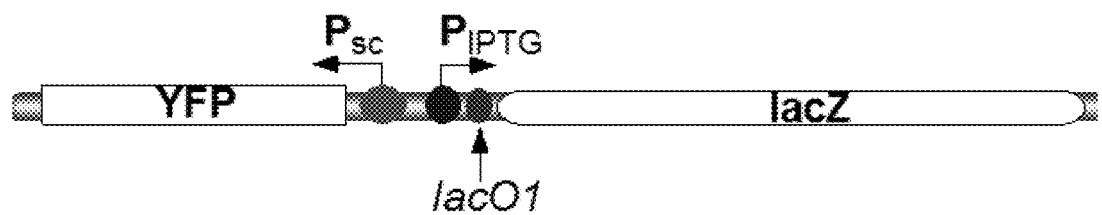
Figure 13E:
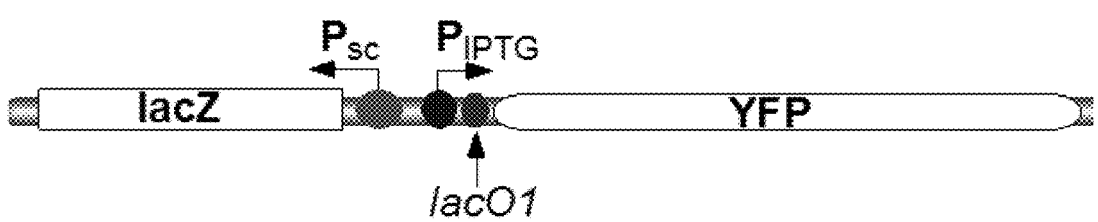

Example 4—Strong Inhibition of the Supercoiling-Sensitive gyrA Promoter by Divergently Coupled Transcription Negative supercoiling also strongly inhibits certain *E. coli* promoters, such as $P_{gyrA}$, in vivo. Whether transcription by *E. coli* RNA polymerase also inhibited a divergently coupled supercoiling sensitive promoter was tested by divergently coupling $P_{gyrA}$ to $P_{T7A1/O4}$ (FIG. 11A). This 5 kb construct was placed into a circular plasmid, a linear plasmid, and the *E. coli* chromosome (FIGS. 11B, 11C, and 11D). How transcription by *E. coli* RNA polymerase inhibited transcription initiated from $P_{gyrA}$ in the topA strain VS111(DE3) ΔlacZ and the wild-type strain MG1655(DE3) ΔlacZ were tested. *E. coli* RNA polymerase substantially inhibited transcription from $P_{gyrA}$ for all three different DNA templates (FIGS. 5B, 12B, and 12D). The inhibition level of $P_{gyrA}$ correlated with the transcription level from $P_{T7A1/O4}$, disregarding the genetic backgrounds of host strains (FIGS. 5 and 12). Several gyrase inhibitors, such as ciprofloxacin, greatly enhanced the expression of firefly luciferase in the presence of IPTG (FIGS. 5D and 12E) although ciprofloxacin inhibited the expression of β-galactosidase (FIG. 5C). The enhancement of the expression of firefly luciferase was specific for gyrase inhibitors. Transcription inhibitors (rifampicin), protein synthesis inhibitors (kanamycin), and cell wall synthesis inhibitors (ampicillin) inhibited the expression of firefly luciferase (FIG. 12F).

This assay can be developed into a unique and specific tool to identify antibiotics targeting bacterial DNA gyrase.

Example 5—Transcription Regulation Via Divergently Coupled Promoters and its Use in Preparation of a Cell, a Polynucleotide and an Assay for Identifying Gyrase Inhibitors Transcription via a promoter potently activates or inhibits a divergently coupled, supercoiling-sensitive promoter, such as $P_{leu-500}$ and $P_{gyrA}$. The activation in certain cases reached 18-fold comparing with transcription in the absence of a divergently coupled transcription unit (FIG. 2). These results can be best explained by the twin supercoiled domain model of transcription. As pointed out by Liu et al., a transcribing RNA polymerase becomes increasingly more difficult to rotate around the axis of the DNA double helix as the size of the growing RNA transcript increases. At a critical point, energetically, it is more feasible for the DNA molecule to rotate around its own helix axis to produce a (+) supercoiled domain ahead of the RNA polymerase and a (−) supercoiled domain behind it.

This disclosure demonstrates that the (−) supercoiled domain behind a transcribing RNA polymerase potently activates $P_{leu-500}$ or inhibits $P_{gyrA}$. $P_{leu-500}$ is a single A-to-G point mutation in the −10 region of the promoter controlling the leu operon, which results in leucine auxotrophy. The AT to GC mutation is expected to increase the energy barrier for the formation of a functional transcription open complex and, as a result, requires (−) supercoiling for its activation (Pruss et al.). $P_{gyrA}$ or $P_{gyrB}$, on the other hand, is inhibited by (−) supercoiling due to the structural properties of DNA elements in and around the promoter (Menzel et al., Straney et al., and Unniraman et al.). TCDS behind a transcribing RNA polymerase provides sufficient energy to activate $P_{leu-500}$ or inhibit $P_{gyrA}$ Or $P_{gyrB}$.

TCDS activates $P_{leu-500}$ in topA strains. However, it was difficult to determine whether transient or global supercoiling contributes the activation because the small circular plasmid DNA templates were usually used in these studies in which the twin-supercoiled-domains produced by transcription can diffuse along the plasmid DNA and therefore cancel each other. Additionally, transcription drives a significant amount of plasmid DNA templates into a hypernegatively superhelical status in topA strains. Therefore, the activation might result from the hypernegative supercoiling that was introduced into the DNA templates. This disclosure demonstrates that transient and dynamic TCDS is responsible for the activation of $P_{leu-500}$. First, TCDS was able to greatly activate $P_{leu-500}$ in the wild-type strain MG1655 (FIGS. 2, 5, and 7). Since MG1655 has all four DNA topoisomerases, the global supercoiling level of DNA templates is not dramatically fluctuated. Additionally, hypernegatively supercoiled DNA cannot be generated in MG1655. This rules out the possibility of building up sufficient permanent supercoiling on the DNA template to activate $P_{leu-500}$. In other words, the activation of $P_{leu-500}$ must stem from transient and dynamic TCDS generated by the divergently coupled transcription unit in MG1655. Second, TCDS was able to potently activate $P_{leu-500}$ on the linear plasmids in *E. coli* cells. Since linear DNA templates cannot be globally supercoiled, the use of linear plasmid DNA templates in *E. coli* wild-type strains demonstrate that transient and dynamic TCDS rather than global supercoiling activates the divergently coupled $P_{leu-500}$. Intriguingly, our results showed that the activation of $P_{leu-500}$ by TCDS is more potent on the chromosome than that on plasmid DNA templates (FIGS. 2 and 7). A possible reason is that unlike plasmid DNA templates, DNA supercoiling domains on the chromosome cannot cancel each other through merging supercoils of opposite signs. In this way, the average lifetime of transient and dynamic TCDS on the chromosome is longer. As a result, the activation of $P_{leu-500}$ would be greater on the chromosome. Nevertheless, this result suggests that the local environment between these two types of DNA templates is quite different.

The disclosure also shows that the activation of $P_{leu-500}$ depends on the promoter strength of the divergently coupled transcription unit (FIGS. 3 and 9). TCDS depends on promoter strength in *E. coli* (Zhi et al.), this disclosure further supports that TCDS is responsible for the activation of $P_{leu-500}$. Interestingly, the activation of $P_{leu-500}$ by TCDS does not require the expression of a membrane-insertion protein in the divergently coupled transcription unit even for $P_{lac}$ that was not able to drive plasmids into hypernegative status in topA strains (Zhi et al.). These results suggest that a transcribing RNA polymerase alone is capable of generating sufficient friction force on E. coli RNA polymerase to produce TCDS on different DNA templates and activate the divergently coupled $P_{leu-500}$ Strong promoters, such as $P_{T7A1/O4}$, on the other hand allow E. coli RNA polymerase to initiate transcription rapidly and multiple RNA polymerases are simultaneously transcribing along the same DNA template. The friction force against multiple RNA polymerases is greatly enhanced and as a result generates significantly more TCDS. This may explain why a strong promoter always yields more activation for $P_{leu-500}$.

Two unique E. coli strains FL1181 and FL1182 (Table 2) are provided that carry a pair of divergently coupled $P_{gyrA}$ and $P_{T7A1/O4}$ controlling the luc and lacZ genes at the attTn7 site of the E. coli chromosome (84 min of the chromosome; (McKenzie et al. and Waddell et al.)). In the presence of IPTG, gyrase inhibitors such as ciprofloxacin specifically enhanced the expression of firefly luciferase for these two E. coli strains (FIGS. 5 and 12E). The model in FIG. 6 explains why in the presence of IPTG ciprofloxacin is able to enhance the expression of firefly luciferase. In the presence of IPTG, transcription initiated from $P_{T7A1/O4}$ produces a significant amount of (−) supercoils behind the RNA polymerase and as a result, inhibits the expression of firefly luciferase by $P_{gyrA}$. However, in the presence of ciprofloxacin, ciprofloxacin stabilizes gyrase-cipro-DNA complex that blocks transcription from $P_{T7A1/O4}$. The (−) supercoiling domain behind the RNA polymerase is not formed. Therefore, the expression of firefly luciferase is greatly "enhanced." This unique property of TCDS can be used to screen and identify antimicrobial compounds targeting bacterial DNA gyrase because only gyrase inhibitors are capable of enhancing the expression of firefly luciferase. Other type of antibiotics all inhibited the expression of firefly luciferase (FIG. 12F).

RNA polymerases are powerful motor proteins that rapidly move along the E. coli chromosome. During the exponential phase when RNA polymerases actively transcribe genes on the chromosome, these motor proteins should produce significant amount of TCDS and remodels the chromosome structure. Indeed, rrnB P1 and P2 promoters were able to greatly activate the divergently coupled $P_{leu-500}$ (FIG. 7). The large amounts of TCDS would be a problem for E. coli cells especially for regions around actively transcribed operons such as the seven ribosomal operons. In other words, how do E. coli cells control the localized DNA supercoiling around these ribosomal operons during the exponential phase? In E. coli, DNA supercoiling status is usually set by the counter actions of DNA topoisomerase I and gyrase. DNA topoisomerase I should be responsible for removing excess (−) supercoils behind a transcribing RNA polymerase. Strong promoters are still able to potently activate the neighboring weak promoters even in the wild-type strain MG1655 (FIGS. 2, 7, and 9), suggesting that E. coli topoisomerases are not the only regulator for control of DNA supercoiling in E. coli. Possibly, E. coli cells also utilize other regulators, such as protein-mediated topological barriers, to control DNA supercoiling at localized levels. For these ribosomal operons, the upstream region of each P1 promoter carries several tandem copies of the FIS binding sites for the activation of the transcription from the P1 promoters. FIS upon binding to the FIS-binding sites may form topological barriers and blocks supercoiling (TCDS) diffusion. In this case, TCDS generated from the strong P1 and P2 promoters activates the P1 promoters. The FIS-mediated topological barriers may prevent TCDS from activating or inhibiting other nearby promoters. In this scenario, the FIS-mediated topological barriers give DNA topoisomerases more time to remove the excess, harmful supercoiling.

REFERENCES

1. Collin et al. (2011), Exploiting bacterial DNA gyrase as a drug target: current state and perspectives, *Appl Microbiol Biotechnol;* 92:479-497.
2. Lacadie, S A, Ibrahim, M M, Gokhale, S A, Ohler, U (2016) Divergent Transcription and Epigenetic Directionality of Human Promoters. FEBS J.
3. Vera, J M, Dowell, R D (2016) Survey of cryptic unstable transcripts in yeast. BMC Genomics 17, 305.
4. Seila, A C, Core, L J, Lis, J T, Sharp, P A (2009) Divergent transcription: a new feature of active promoters. Cell Cycle 8, 2557-2564.
5. Beck, C F, Warren, R A (1988) Divergent promoters, a common form of gene organization. Microbiol. Rev. 52, 318-326.
6. Yamada, M, Kabir, M S, Tsunedomi, R (2003) Divergent promoter organization may be a preferred structure for gene control in *Escherichia coli*. J. Mol. Microbiol. Biotechnol. 6, 206-210.
7. Neil, H et al. (2009) Widespread bidirectional promoters are the major source of cryptic transcripts in yeast. Nature 457, 1038-1042.
8. Xu, Z et al. (2009) Bidirectional promoters generate pervasive transcription in yeast. Nature 457, 1033-1037.
9. Proudfoot, N, Gullerova, M (2007) Gene silencing CUTs both ways. Cell 131, 649-651.
10. Seila, A C et al. (2008) Divergent transcription from active promoters. Science 322, 1849-1851.
11. Core, L J, Waterfall, J J, Lis, J T (2008) Nascent RNA sequencing reveals widespread pausing and divergent initiation at human promoters. Science 322, 1845-1848.
12. Sigova, A A et al. (2013) Divergent transcription of long noncoding RNA/mRNA gene pairs in embryonic stem cells. Proc. Natl. Acad. Sci. USA 110, 2876-2881.
13. Scruggs, B S et al. (2015) Bidirectional Transcription Arises from Two Distinct Hubs of Transcription Factor Binding and Active Chromatin. Mol. Cell 58, 1101-1112.
14. Duttke, S H et al. (2015) Human promoters are intrinsically directional. Mol. Cell 57, 674-684.
15. Marquardt, S et al. (2014) A chromatin-based mechanism for limiting divergent noncoding transcription. Cell 157, 1712-1723.
16. Kouzine, F et al. (2013) Transcription-dependent dynamic supercoiling is a short-range genomic force. Nat. Struct. Mol. Biol. 20, 396-403.
17. Naughton, C et al. (2013) Transcription forms and remodels supercoiling domains unfolding large-scale chromatin structures. Nat. Struct. Mol. Biol. 20, 387-395.
18. Liu, L F, Wang, J C (1987) Supercoiling of the DNA template during transcription. Proc. Natl. Acad. Sci. U.S.A 84, 7024-7027.
19. Rhee, K Y et al. (1999) Transcriptional coupling between the divergent promoters of a prototypic LysR-type regulatory system, the ilvYC operon of *Escherichia coli*. Proc. Natl. Acad. Sci. U.S.A 96, 14294-14299.
20. Opel, M L, Hatfield, G W (2001) DNA supercoiling-dependent transcriptional coupling between the divergently transcribed promoters of the ilvYC operon of *Escherichia coli* is proportional to promoter strengths and transcript lengths. Mol. Microbiol. 39, 191-198.

21. Lilley, D M, Higgins, C F (1991) Local DNA topology and gene expression: the case of the leu-500 promoter. Mol. Microbiol. 5, 779-783.
22. Chen, D, Bowater, R, Dorman, C J, Lilley, D M (1992) Activity of a plasmid-borne leu-500 promoter depends on the transcription and translation of an adjacent gene. Proc. Natl. Acad. Sci. U.S.A 89, 8784-8788.
23. Tan, J, Shu, L, Wu, H Y (1994) Activation of the leu-500 promoter by adjacent transcription. J. Bacteriol. 176, 1077-1086.
24. Wu, H Y, Tan, J, Fang, M (1995) Long-range interaction between two promoters: activation of the leu-500 promoter by a distant upstream promoter. Cell 82, 445-451.
25. Fang, M, Wu, H Y (1998) A promoter relay mechanism for sequential gene activation. J. Bacteriol. 180, 626-633.
26. Fang, M, Wu, H Y (1998) Suppression of leu-500 mutation in topA+ *Salmonella* typhimurium strains. The promoter relay at work. J. Biol. Chem. 273, 29929-29934.
27. El, H D, Bossi, L (2000) Activation and silencing of leu-500 promoter by transcription-induced DNA supercoiling in the *Salmonella* chromosome. Mol. Microbiol. 37, 583-594.
28. Chen, C C, Wu, H Y (2003) Transcription-driven DNA supercoiling and gene expression control. Front Biosci. 8, d430-d439.
29. Wu, H Y, Fang, M (2003) DNA supercoiling and transcription control: a model from the study of suppression of the leu-500 mutation in *Salmonella typhimurium* topA-strains. Prog. Nucleic Acid Res. Mol. Biol. 73, 43-68.
30. Fulcrand, G et al. (2016) DNA supercoiling, a critical signal regulating the basal expression of the lac operon in *Escherichia coli*. Sci. Rep. 6, 19243.
31. Zhi, X, Leng, F (2013) Dependence of transcription-coupled DNA supercoiling on promoter strength in *Escherichia coli* topoisomerase I deficient strains. Gene 514, 82-90.
32. Samul, R, Leng, F (2007) Transcription-coupled hypernegative supercoiling of plasmid DNA by T7 RNA polymerase in *Escherichia coli* topoisomerase I-deficient strains. J. Mol. Biol. 374, 925-935.
33. McKenzie, G J, Craig, N L (2006) Fast, easy and efficient: site-specific insertion of transgenes into enterobacterial chromosomes using Tn7 without need for selection of the insertion event. BMC. Microbiol. 6, 39.
34. Waddell, C S, Craig, N L (1989) Tn7 transposition: recognition of the attTn7 target sequence. Proc. Natl. Acad. Sci. U.S.A 86, 3958-3962.
35. Miller, J. H. (1972) Experiments in Molecular Genetics (Cold Spring Harbor Laboratory, Cold Spring Harbor, N.Y.).
36. Wu, H Y, Shyy, S H, Wang, J C, Liu, L F (1988) Transcription generates positively and negatively supercoiled domains in the template. Cell 53, 433-440.
37. Tsao, Y P, Wu, H Y, Liu, L F (1989) Transcription-driven supercoiling of DNA: direct biochemical evidence from in vitro studies. Cell 56, 111-118.
38. Nelson, P (1999) Transport of torsional stress in DNA. Proc. Natl. Acad. Sci. U.S.A 96, 14342-14347.
39. Leng, F, McMacken, R (2002) Potent stimulation of transcription-coupled DNA supercoiling by sequence-specific DNA-binding proteins. Proc. Natl. Acad. Sci. U.S.A 99, 9139-9144.
40. Mielke, S P et al. (2004) Transcription-driven twin supercoiling of a DNA loop: a Brownian dynamics study. J. Chem. Phys. 121, 8104-8112.
41. Mukai, F H, Margolin, P (1963) ANALYSIS OF UNLINKED SUPPRESSORS OF AN O degrees MUTATION IN SALMONELLA. Proc. Natl. Acad. Sci. U.S.A 50, 140-148.
42. Dubnau, E, Margolin, P (1972) Suppression of promoter mutations by the pleiotropic supx mutations. Mol. Gen. Genet. 117, 91-112.
43. Pruss, G J, Drlica, K (1985) DNA supercoiling and suppression of the leu-500 promoter mutation. J. Bacteriol. 164, 947-949.
44. Menzel, R, Gellert, M (1987) Modulation of transcription by DNA supercoiling: a deletion analysis of the *Escherichia coli* gyrA and gyrB promoters. Proc. Natl. Acad. Sci. U.S.A 84, 4185-4189.
45. Straney, R, Krah, R, Menzel, R (1994) Mutations in the −10 TATAAT sequence of the gyrA promoter affect both promoter strength and sensitivity to DNA supercoiling. J. Bacteriol. 176, 5999-6006.
46. Unniraman, S, Nagaraja, V (2001) Axial distortion as a sensor of supercoil changes: a molecular model for the homeostatic regulation of DNA gyrase. J. Genet. 80, 119-124.
47. Pruss, G J (1985) DNA topoisomerase I mutants. Increased heterogeneity in linking number and other replicon-dependent changes in DNA supercoiling. J. Mol. Biol. 185, 51-63.
48. Snoep, J L et al. (2002) DNA supercoiling in *Escherichia coli* is under tight and subtle homeostatic control, involving gene-expression and metabolic regulation of both topoisomerase I and DNA gyrase. Eur. J. Biochem. 269, 1662-1669.
49. Zechiedrich, E L et al. (2000) Roles of topoisomerases in maintaining steady-state DNA supercoiling in *Escherichia coli*. J. Biol. Chem. 275, 8103-8113.
50. Deneke, J, Ziegelin, G, Lurz, R, Lanka, E (2000) The protelomerase of temperate *Escherichia coli* phage N15 has cleaving-joining activity. Proc. Natl. Acad. Sci. U. S. A 97, 7721-7726.
51. Ma, J, Bai, L, Wang, M D (2013) Transcription under torsion. Science 340, 1580-1583.
52. Ma, J, Wang, M D (2014) RNA polymerase is a powerful torsional motor. Cell Cycle 13, 337-338.
53. Dennis, P P, Ehrenberg, M, Bremer, H (2004) Control of rRNA synthesis in *Escherichia coli*: a systems biology approach. Microbiol. Mol. Biol. Rev. 68, 639-668.
54. Appleman, J A, Ross, W, Salomon, J, Gourse, R L (1998) Activation of *Escherichia coli* rRNA transcription by FIS during a growth cycle. J. Bacteria 180, 1525-1532.
55. Leng, F, Chen, B, Dunlap, D D (2011) Dividing a supercoiled DNA molecule into two independent topological domains. Proc. Natl. Acad. Sci. U.S.A 108, 19973-19978.

We claim:

1. A linear DNA construct comprising:
   i) a first inducible promoter under the control of an inducer and operably linked to a first gene and at least one terminator, and
   ii) a second promoter operably linked to a second gene;
   wherein the first promoter is $P_{T7lac}$, $P_{trc}$, $P_{lac}$, $P_{T7A1/O4}$, $P_{lacUV5}$, $P_{rhaBAD}$, $P_{ara}$, $P_{tetA}$, $P_{recA}$, $P_{phoA}$, $P_{trp}$, $P_{nar}$, $P_{PL}$, $P_{espA}$, $P_{proU}$, or $P_{est-4}$ and the second promoter is $P_{gyrA}$ or $P_{gyrB}$;
   wherein the second promoter is divergently coupled to the first promoter such that:
   a) the first promoter is located between the second promoter and the first gene;
   b) the second promoter is located between the first promoter and the second gene;
   c) at least the first promoter is heterologous to the first gene or the second promoter is heterologous to the second gene; and
   d) no additional promoter is positioned between the first promoter and the second promoter;
   wherein, when the linear DNA construct is incorporated in a linear or circular DNA vector or into genomic DNA in a prokaryotic host cell, the first and the second promoters initiate transcription in opposite directions to each other; transcription of the first gene under the control of the first promoter causes negative supercoiling of the second promoter; and said negative supercoiling of the second promoter inhibits transcription of the second gene from the second promoter.

2. The DNA construct of claim 1, wherein the DNA construct further comprises one or more of: a terminator for the second gene, a selectable marker, an origin of replication for replication in a prokaryotic cell and/or a eukaryotic cell, and a multiple cloning site.

3. The DNA construct of claim 1, wherein the first gene encodes for a first peptide and the second gene encodes for a second peptide.

4. The DNA construct of claim 1, wherein only the first gene or only the second gene encodes for a marker protein.

5. A cell or a culture of the cell, wherein the cell comprises the DNA construct of claim 1.

6. The cell of claim 5, wherein the cell is a prokaryotic cell.

7. The cell of claim 5, wherein the construct is incorporated into extra-chromosomal genetic material.

8. The cell of claim 5, wherein the construct is integrated into the genome of the cell.

9. A linear NA construct comprising:
   i) a first promoter operably linked to a first gene, and
   ii) a second promoter operably linked to a second gene;
   wherein the first promoter is $P_{T7lac}$, $P_{lac}$, $P_{T7A1/O4}$, or $P_{lacUV5}$, and the second promoter is $P_{gyrA}$ or $P_{gyrB}$;
   wherein the second promoter is divergently coupled to the first promoter such that:
   a) the first promoter is located between the second promoter and the first gene;
   b) the second promoter is located between the first promoter and the second gene;
   c) at least the first promoter is heterologous to the first gene or the second promoter is heterologous to the second gene; and
   d) no additional promoter is positioned between the first promoter and the second promoter;
   wherein, when the linear DNA construct is incorporated in a linear or circular DNA vector or into genomic DNA in a prokaryotic host cell, the first and the second promoters initiate transcription in opposite directions to each other; transcription of the first gene under the control of the first promoter causes negative supercoiling of the second promoter; and said negative supercoiling of the second promoter inhibits transcription of the second gene from the second promoter.

10. The DNA construct according to claim 1, wherein the first promoter is separated by no more than 92 bp from the second promoter.

11. The DNA construct according to claim 9, wherein the first promoter is separated by no more than 92 bp from the second promoter.

* * * * *

SEQUENCE LISTING

<160> NUMBER OF SEQ ID NOS: 13

<210> SEQ ID NO 1

-continued

```
<211> LENGTH: 146
<212> TYPE: DNA
<213> ORGANISM: Artificial
<220> FEATURE:
<223> OTHER INFORMATION: divergently coupled leu-500 promoter with
      PT7A1/O4 promoter

<400> SEQUENCE: 1
ttagtggcac tggatatgcc gtttaatgtc aactctattt tctgggatcc caaatagggg    60
ttccgcgcac atttccccga aaagtgccac ctgacgtgaa ttcaaaaaga gtattgactt   120
gtgagcggat aacaatgata cttaca                                        146

<210> SEQ ID NO 2
<211> LENGTH: 43
<212> TYPE: DNA
<213> ORGANISM: Escherichia coli

<400> SEQUENCE: 2
agtattgact tgtgagcgga taacaatgat acttacagcc atc                      43

<210> SEQ ID NO 3
<211> LENGTH: 61
<212> TYPE: DNA
<213> ORGANISM: Escherichia coli

<400> SEQUENCE: 3
gctgttgaca attaatcatc ggctcgtata atgtgtggaa ttgtgagcgg ataacaattt    60
c                                                                    61

<210> SEQ ID NO 4
<211> LENGTH: 63
<212> TYPE: DNA
<213> ORGANISM: Escherichia coli

<400> SEQUENCE: 4
aggctttaca ctttatgctt ccggctcgta taatgtgtgg aattgtgagc ggataacaat    60
ttc                                                                  63

<210> SEQ ID NO 5
<211> LENGTH: 63
<212> TYPE: DNA
<213> ORGANISM: Escherichia coli

<400> SEQUENCE: 5
aggctttaca ctttatgctt ccggctcgta tgttgtgtgg aattgtgagc ggataacaat    60
ttc                                                                  63

<210> SEQ ID NO 6
<211> LENGTH: 155
<212> TYPE: DNA
<213> ORGANISM: Artificial
<220> FEATURE:
<223> OTHER INFORMATION: divergently coupled gyrA promoter with PT7A1/O4
      promoter

<400> SEQUENCE: 6
aaattataac acagccgcgc agtttgaggt aaacctatac gctttattca catccggatc    60
ccaaataggg gttccgcgca catttccccg aaaagtgcca cctgacgtga attcaaaaag   120
agtattgact tgtgagcgga taacaatgat actta                              155
```

```
<210> SEQ ID NO 7
<211> LENGTH: 23
<212> TYPE: DNA
<213> ORGANISM: Artificial
<220> FEATURE:
<223> OTHER INFORMATION: forward primer for amplification of luc gene

<400> SEQUENCE: 7
aacaacggcg gcgggaagtt cac                                              23

<210> SEQ ID NO 8
<211> LENGTH: 23
<212> TYPE: DNA
<213> ORGANISM: Artificial
<220> FEATURE:
<223> OTHER INFORMATION: reverse primer for amplification of luc gene

<400> SEQUENCE: 8
gggacgaaga cgaacacttc ttc                                              23

<210> SEQ ID NO 9
<211> LENGTH: 20
<212> TYPE: DNA
<213> ORGANISM: Artificial
<220> FEATURE:
<223> OTHER INFORMATION: forward primer for amplification of 16s rRNA
      gene

<400> SEQUENCE: 9
agttatcccc ctccatcagg                                                  20

<210> SEQ ID NO 10
<211> LENGTH: 20
<212> TYPE: DNA
<213> ORGANISM: Artificial
<220> FEATURE:
<223> OTHER INFORMATION: reverse primer for amplification of 16s rRNA
      gene

<400> SEQUENCE: 10
tgcaagtcga acggtaacag                                                  20

<210> SEQ ID NO 11
<211> LENGTH: 23
<212> TYPE: DNA
<213> ORGANISM: Artificial
<220> FEATURE:
<223> OTHER INFORMATION: forward primer for amplification of lacZ gene

<400> SEQUENCE: 11
attatggccc acaccagtgg cgc                                              23

<210> SEQ ID NO 12
<211> LENGTH: 21
<212> TYPE: DNA
<213> ORGANISM: Artificial
<220> FEATURE:
<223> OTHER INFORMATION: reverse primer for amplification of lacZ gene

<400> SEQUENCE: 12
tgacgggctc caggagtcgt c                                                21

<210> SEQ ID NO 13
<211> LENGTH: 81
<212> TYPE: DNA
<213> ORGANISM: Escherichia coli
```

```
<400> SEQUENCE: 13
atagacatgt cggacgaaaa ttcgaagatg tttaccgtgg aaaagggtaa aataacggat        60
taacccaagt ataaatgagc g                                                 81
```